US009931123B2

(12) United States Patent
Blake, III

(10) Patent No.: US 9,931,123 B2
(45) Date of Patent: Apr. 3, 2018

(54) SURGICAL CLIP APPLIER

(76) Inventor: Joseph W Blake, III, New Canaan, CT (US)

( * ) Notice: Subject to any disclaimer, the term of this patent is extended or adjusted under 35 U.S.C. 154(b) by 172 days.

(21) Appl. No.: 13/385,760

(22) Filed: Mar. 6, 2012

(65) Prior Publication Data

US 2013/0165951 A1    Jun. 27, 2013

Related U.S. Application Data

(60) Provisional application No. 61/630,915, filed on Dec. 21, 2011.

(51) Int. Cl.
*A61B 17/10* (2006.01)
*A61B 17/128* (2006.01)
*A61B 17/00* (2006.01)

(52) U.S. Cl.
CPC .. *A61B 17/1285* (2013.01); *A61B 2017/0046* (2013.01)

(58) Field of Classification Search
CPC ................... A61B 17/1285; A61B 2017/0046

USPC ......................................... 606/143, 242, 243
See application file for complete search history.

(56) References Cited

U.S. PATENT DOCUMENTS

| 5,431,668 | A  | * | 7/1995 | Burbank et al. | ............... 606/143 |
| 6,423,079 | B1 | * | 7/2002 | Blake, III | ...................... 606/143 |
| 2008/0027466 | A1 | * | 1/2008 | Vitali et al. | .................... 606/143 |
| 2009/0138033 | A1 | * | 5/2009 | Blake, III | ..................... 606/184 |

* cited by examiner

*Primary Examiner* — Gregory Anderson
*Assistant Examiner* — Sarah Simpson
(74) *Attorney, Agent, or Firm* — Patrick J. Walsh

(57) ABSTRACT

A surgical clip applier with scissor-type operating handle and clip applying cartridge in which handle has housing of upper and lower shells that defines socket for receiving cartridge, includes a lever arm actuated linear translator for linear reciprocating movement delivered to the cartridge, and an anti-backup mechanism for full forward and release strokes of the handle, and in which cartridge includes jaws for applying clips, safety means to ensure opening of jaws for each cycle, a puller bar for receiving motion from handle and timing of jaw operation to clip feed, a magazine for feeding clips to jaws in proper sequence, and a lockout mechanism to render applier inoperative after using last clip.

1 Claim, 14 Drawing Sheets

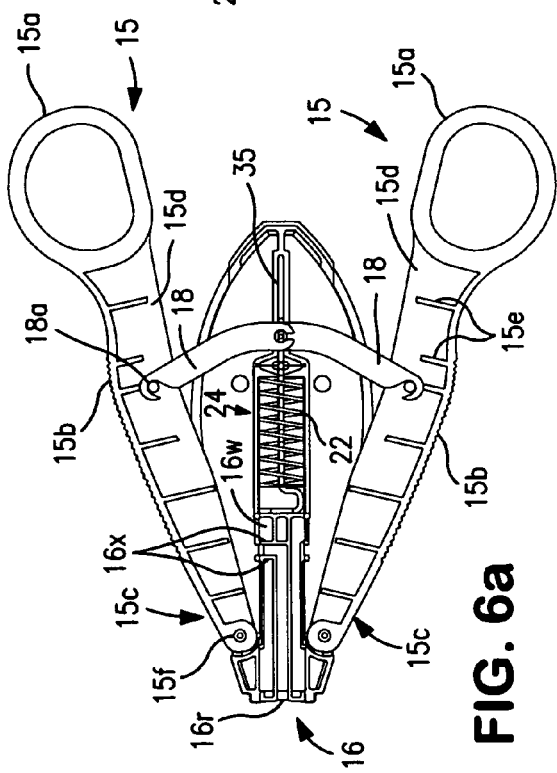

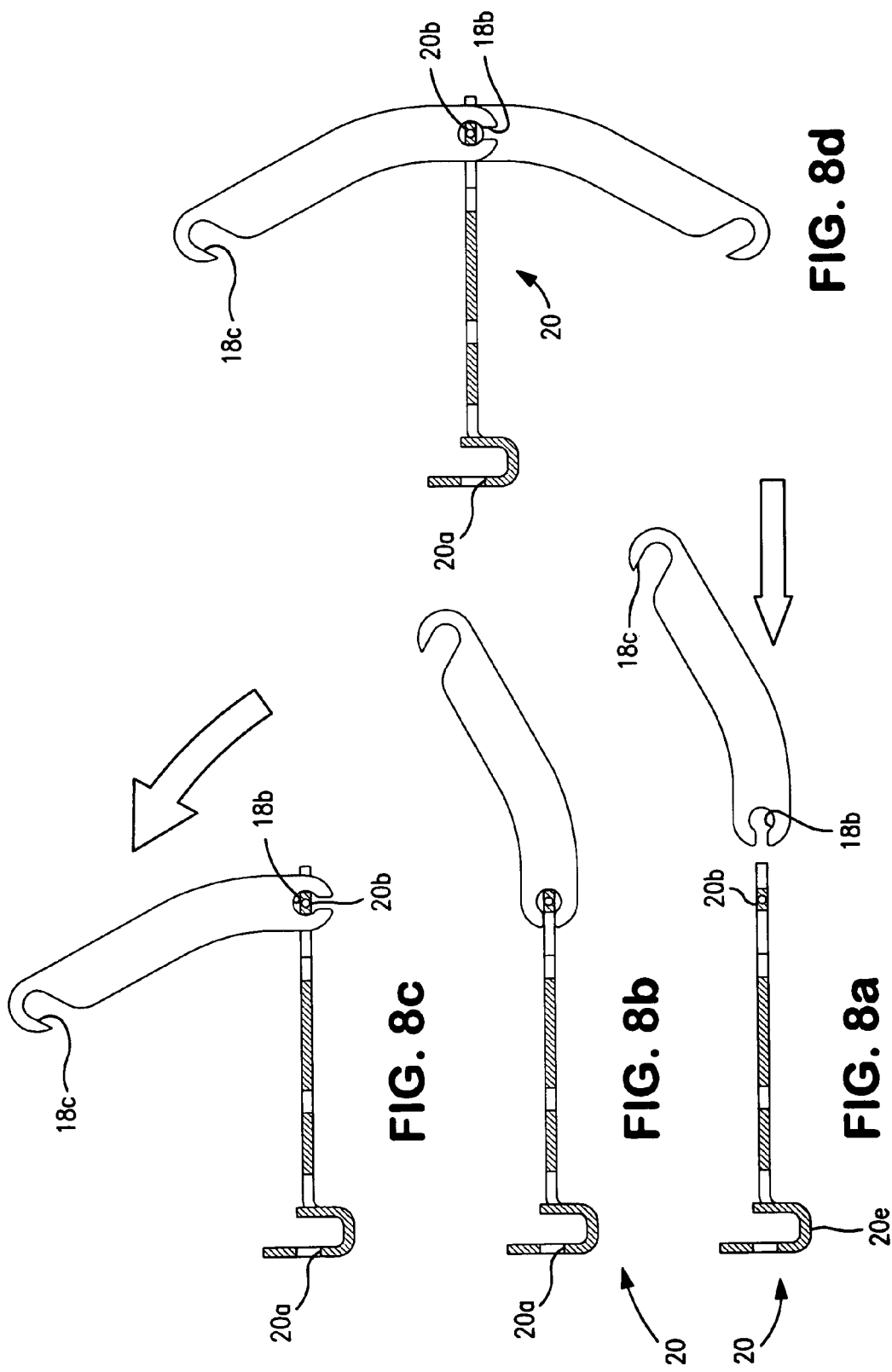

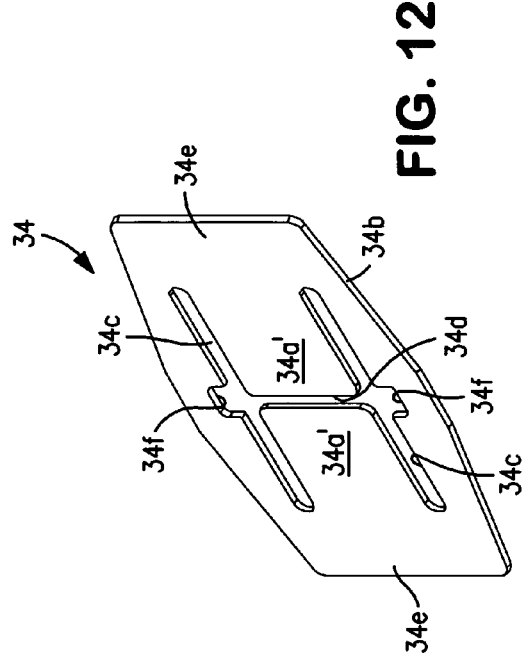
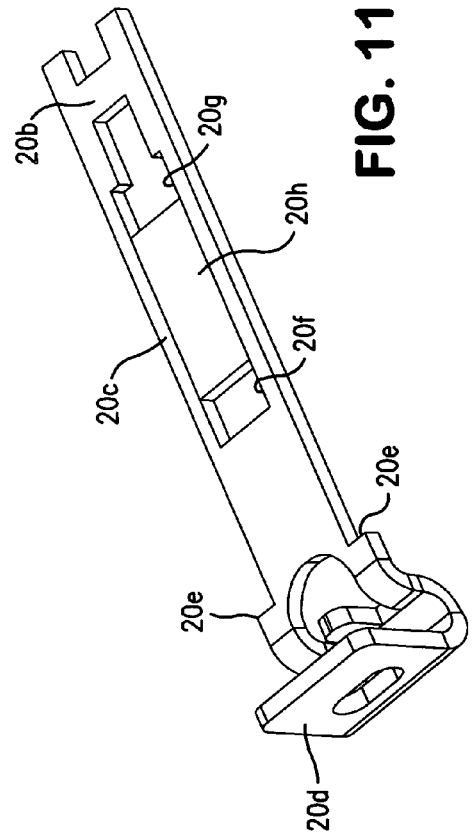
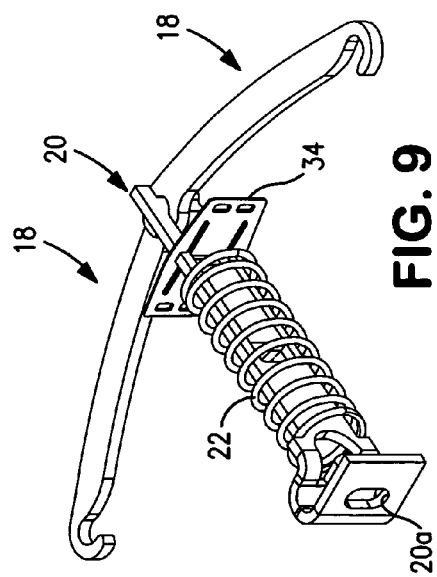
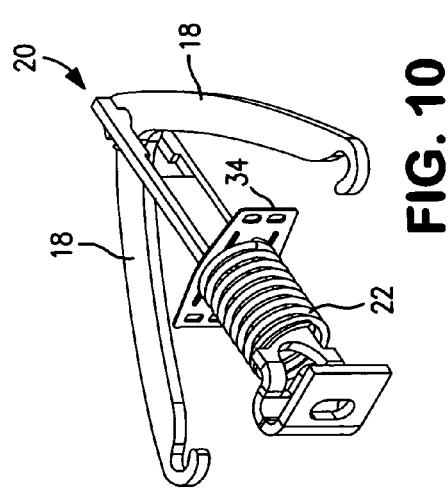

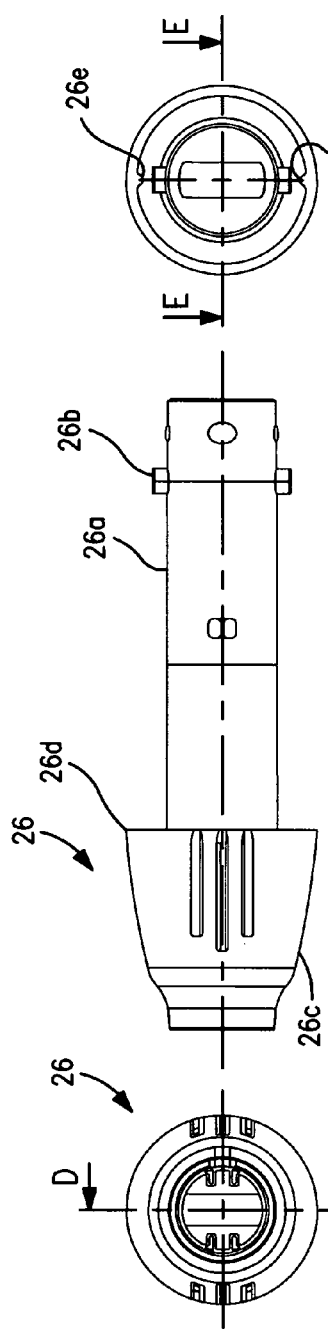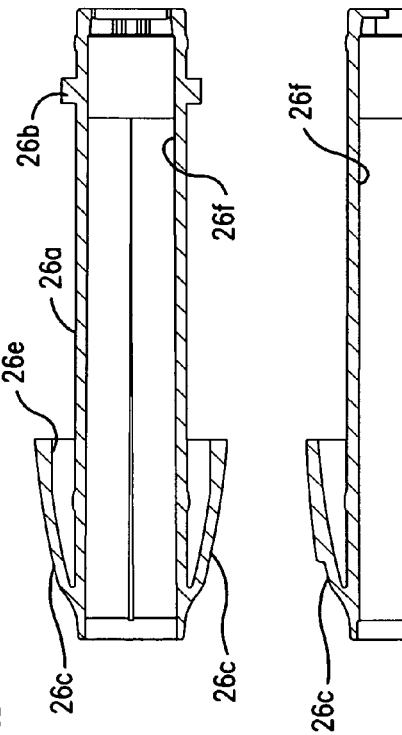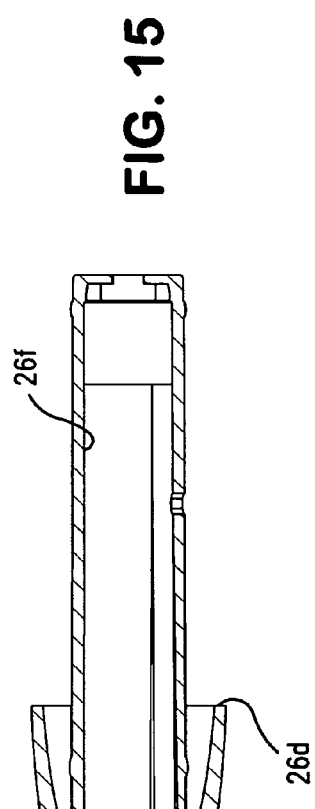
FIG. 13c
FIG. 14
FIG. 15
FIG. 13a
FIG. 13b

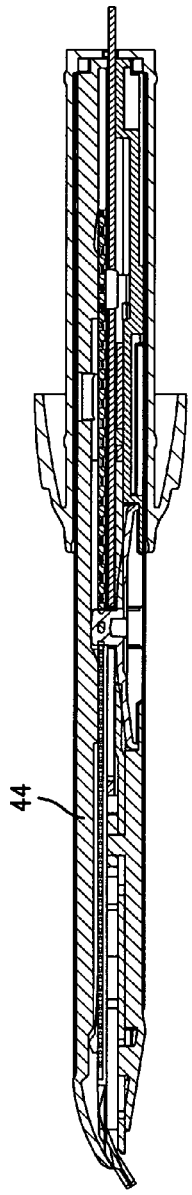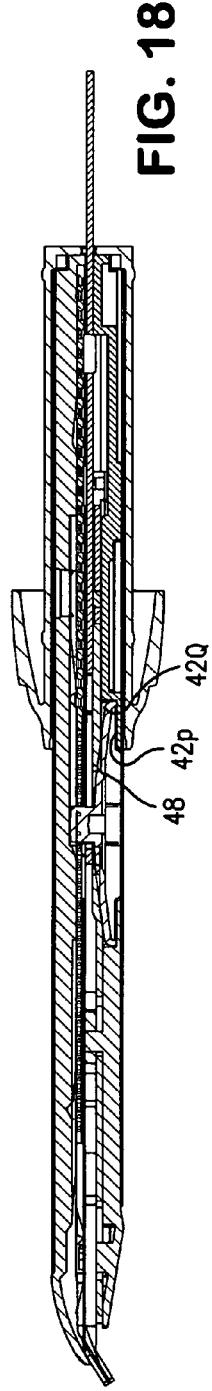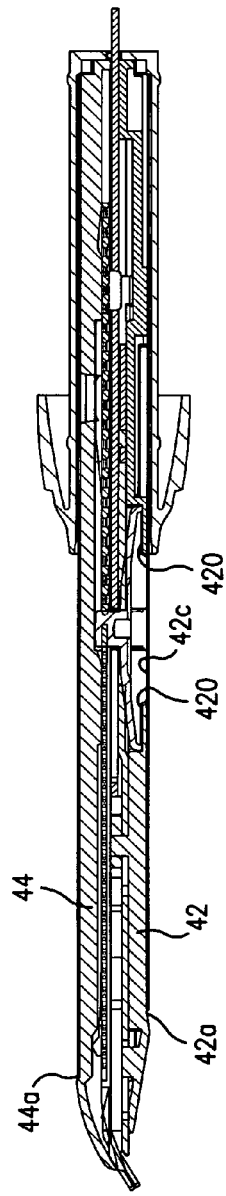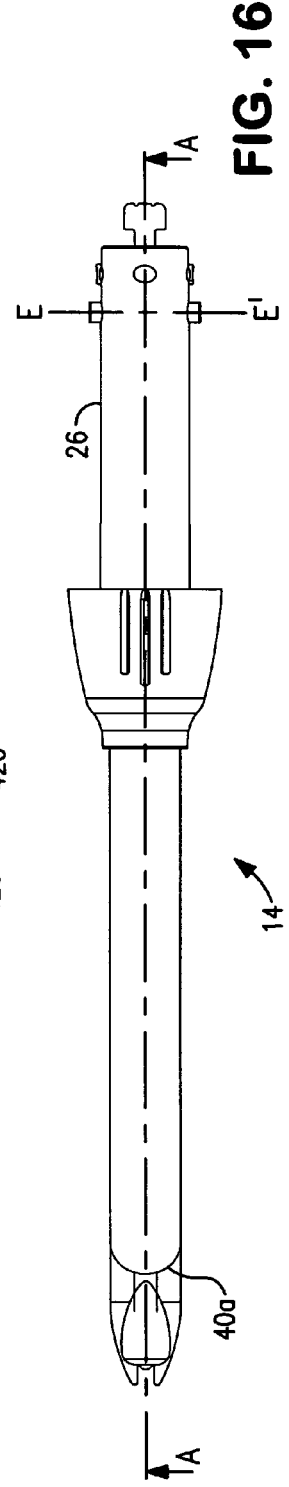

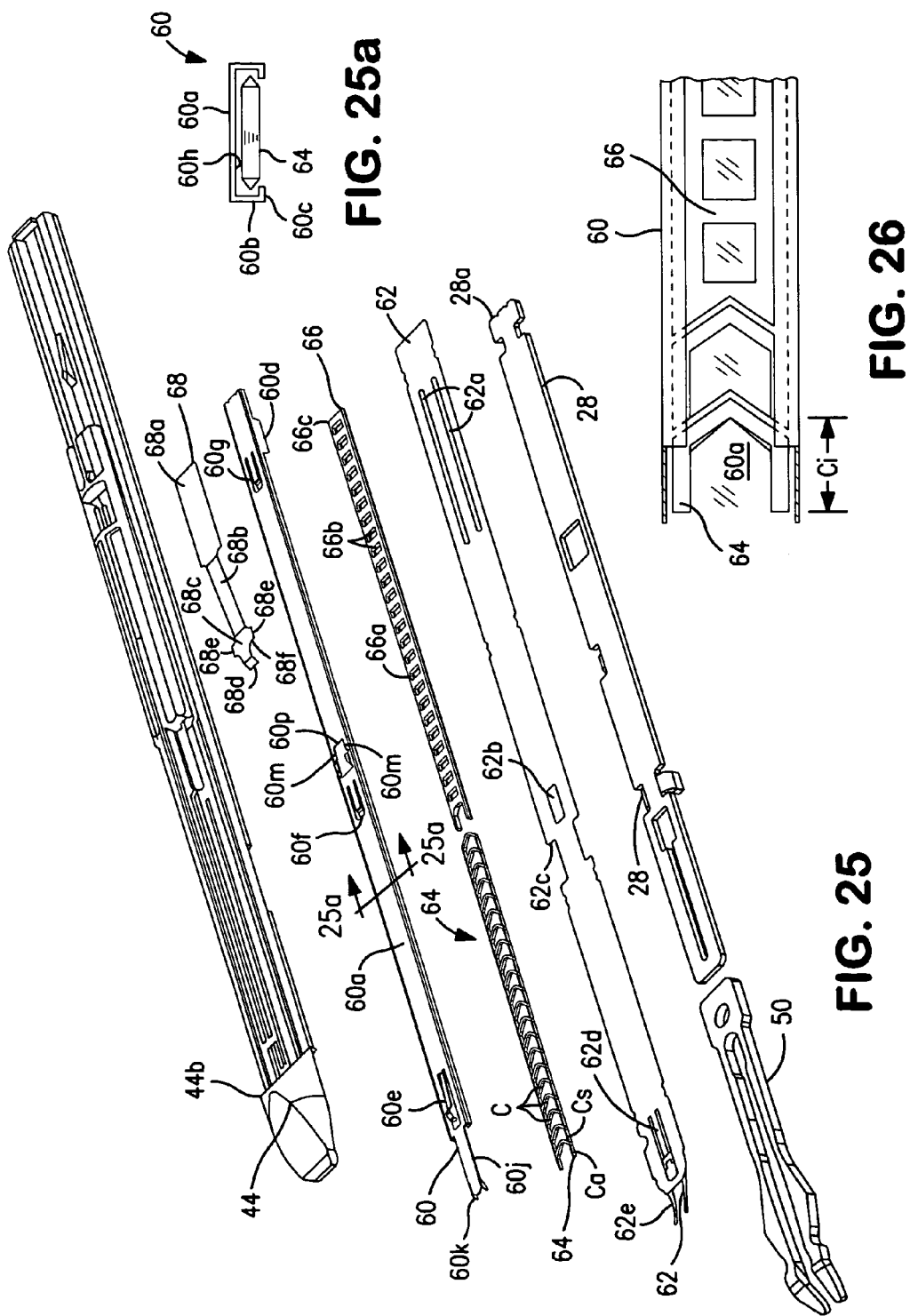

SURGICAL CLIP APPLIER

PRIORITY

This application claims priority of U.S. Provisional Patent Application Ser. No. 61/630,915 filed Dec. 21, 2011.

FIELD OF THE INVENTION

The present invention relates to surgical clip appliers as an instrument having a supply of clips for closing severed blood vessels and other fluid carrying ducts in surgical procedures.

BACKGROUND OF THE INVENTION

There are many different designs for surgical clip appliers for a variety of surgical procedures including both open and laparoscopic surgery.

This invention comprises improvements in repeating multi-clip appliers of the kind described and claimed in my U.S. Pat. Nos. 6,423,079 and 6,869,435.

The '079 patent describes a clip applier with an operating handle and clip applying mechanism defining an operating cycle in which a clip is applied in surgery and the clip applier is reloaded with a single clip from a clip supply channel for clip application in the next cycle. The applier provides a moveable clip supply channel containing a line of clips that are released seriatim.

Clip crimping jaws apply a clip with a rearward movement of a cam member thereby allowing the functions of clip loading and jaw closure to be coordinated and operated by a single sliding bar moving reciprocally to load and fire clips.

The clip actuating mechanism includes a combined actuating bar and in-line clip supply channel together with clip indexing mechanisms arranged so that with a squeeze of the operating levers, the actuating bar moves rearward in the appliance to apply a clip in surgery, capture the next in-line clip, index a line of clips rearward away from the clip jaws; and that with release of the operating levers, the jaws open, the next in-line clip is loaded into the jaws, the second next in-line clip is separated from the line, and the clip indexing movement is reset for the next cycle.

My '435 patent discloses a repeating multi-clip applier having an operating handle housing and a removable and disposable clip applying cartridge.

The operating handle housing accommodates a pistol grip set of handles which provide linear reciprocating motion by means of a spring biased translator slide for actuating the clip applying mechanism within the cartridge. The operating handle housing includes a rotary thumb wheel hub and rotatable drum subassembly which receive the clip cartridge for 360° rotation about the cartridge axis and which link the cartridge clip applying mechanism to the translator slide.

The operating handle housing accommodates an anti-backup mechanism to prevent a partial pull and release of the operating handles to avoid a well-known hazard that can occur when clip appliers are used in surgery. The hazard is that of dropping and losing a partially closed clip in a surgical site. The anti-backup mechanism avoids the hazard by preventing handle release before a clip in the instrument jaws is fully closed and applied at a surgical site.

The '435 clip applying mechanism includes a combined actuating bar and in-line clip supply cartridge together with clip advancing mechanisms arranged so that with a squeeze of the operating handle, the actuating bar moves rearward in the instrument to close its jaws to apply a clip in surgery, capture the next in-line clip, retain and move a line of clips rearward away from the clip jaws, and that with release of the operating levers, the jaws open, the next in-line clip is loaded into the jaws, the second next in-line clip is separated from the line, and the clip retaining means is reset for the next cycle.

In practice, clip cartridges are ordinarily used a single time and discarded. Operating handles, on the other hand, may be disposed of after use with a single cartridge, or may be used with a plurality of cartridges in a single surgical procedure and then discarded, or may be autoclaved after each surgical procedure and used over and over again.

SUMMARY OF THE INVENTION

A preferred embodiment of repeating multi-clip applier according to the present invention comprises an instrument having an operating handle housing and a removable and disposable clip applying cartridge. A full squeeze and release of operating handles applies a clip to a surgical site and reloads another clip into clip applying jaws of the instrument.

The operating handle housing preferably comprises a scissors grip handle which imparts linear reciprocating motion of fixed excursion to the clip applying mechanism within the cartridge. The fixed excursion is determined by a spring biased linear actuator. The linear actuator within the operating handle connects to an end of a puller bar of the clip cartridge mechanism wherein the puller bar receives and transmits linear reciprocating motion to operating components of the cartridge.

The operating handle housing accommodates an anti-backup mechanism to prevent a partial pull and release and to prevent a full pull and partial release of operating handles. As noted above, a partial pull and release creates the hazard of the clip applier releasing and dropping a partially closed clip into a surgical site. Furthermore, partial release can result in double loading clips into crimping jaws, a condition that jams proper functioning of the applier mechanism.

The anti-backup mechanism comprises a toggle spring with spaced confronting spring tabs in fixed position within the handle housing for cooperation with anti-backup surfaces of the linear actuator. When the scissor handles are actuated by squeezing them together, the anti-backup surfaces pass into the space between the toggle spring tabs preventing handle release until the spring tab edges enter an opening (marking one end point of linear excursion) formed in the anti-backup surfaces.

When in the opening, the spring tabs can toggle over so as to accommodate return excursion of the linear actuator. The other end point of return excursion is marked by another opening formed in the anti-backup surfaces, where linear actuator is released for a return stroke.

The cartridge comprises:

(i) a housing consisting of outer sleeve with chassis and cover providing a stationary base for operating cartridge members;

(ii) a puller bar as prime mover that receives from the operating handle and transmits to operating cartridge members a linear reciprocating motion of fixed excursion from which movement of individual cartridge members is derived;

(iii) a first set of cartridge members driven by the puller bar that actuate clip applying jaws for applying a clip in surgery;

(iv) a second set of cartridge members driven by the puller bar for handling surgical clips for the purpose of feeding the clips one at a time into the clip applying jaws;

(v) an arrangement of first and second set members cooperating in timed sequence such that in an operating cycle of the instrument during which the scissor handles undergo full pull and full release, a clip is applied in surgery and the next clip is advanced into the applier jaws;

(vi) a lockout mechanism that inhibits clip applier operation after the last remaining clip in the clip channel has been used in surgery; and, (vii) a tissue stop for properly positioning clip and tissue at that moment when the clip is applied to tissue in surgery.

The clip applier has a novel mechanism with minimal complexity especially suited for a disposable cartridge for fixed handle appliances. The clip applier employs low operating force without recoil and is adaptable for use as a quick snap-in disposable cartridge with a fixed operating handle. The simplified mechanism reduces tooling and assembly requirements, provides high operating reliability at lower product cost.

Specific examples are included in the following description for purposes of clarity, but various details can be changed within the scope of the present invention.

OBJECTS OF THE INVENTION

An object of the invention is to provide a novel clip applicator with minimum complexity and with adaptability to a complete range of clip sizes used in open and laparoscopic surgery.

Another object of the invention is to provide a clip applicator adaptable for use with a replaceable cartridge.

Another object of the invention is to provide a clip applicator having an operating handle that provides anti-backup linear reciprocating motion.

Another object of the invention is to provide a clip applicator in which clip feed and applying mechanisms are driven by an actuator having a linear reciprocating motion generated by operating handles.

Another object of the invention is to provide a surgical clip applier with an anti-backup means to prevent release of partially closed clips at a surgical site.

Another object of the invention is to provide a clip applying cartridge which can be used with various operating handle configurations including pistol grip, scissor type, and surgical robot.

Other and further objects of the invention will become apparent with an understanding of the following detailed description of the invention or upon employment of the invention in practice.

BRIEF DESCRIPTION OF THE DRAWING

A preferred embodiment of the invention has been chosen for detailed description to enable those having ordinary skill in the art to which the invention appertains to readily understand how to construct and use the invention and is shown in the accompanying drawing in which:

FIGS. 6a-b are plan views of applicator handle of FIG. 1 showing arrangement of linear actuator, handle connecting links, handle main spring, and anti-backup mechanism within handle housing, with handle shown in release and closed positions, respectively.

FIGS. 7a-d are plan view; side elevation view; section view taken along line c-c of FIG. 7b; and front view of linear actuator of FIGS. 2 and 3 and 6a-b.

FIGS. 8a-d are plan views of linear actuator of FIG. 7c showing connection with handle connecting links.

FIG. 9 is a perspective view of handle components including linear actuator, anti-backup mechanism, and handle links in release position of handle lever arms.

FIG. 10 is a perspective view of handle components including linear actuator, anti-backup mechanism, and handle links in squeeze position of handle lever arms.

FIG. 11 is a perspective view of linear actuator.

FIG. 12 is a perspective view of anti-backup spring.

FIGS. 13a-c are top plan view, front elevation, and rear elevation of cartridge end cap for mounting cartridge to handle.

FIG. 14 is a section view along line D-D of cartridge end cap of FIG. 13b.

FIG. 15 is a section view along line E-E of cartridge end cap of FIG. 13c.

FIG. 16 is a plan view of cartridge and cartridge end cap of applicator of FIG. 1.

FIGS. 17-19 are side elevation section views of cartridge and cartridge cap of FIG. 16 showing position of cartridge internal components as cartridge pull bar travels full linear excursion.

FIG. 25 is an enlarged perspective view of second set of cartridge members for keeping and delivering clips to applicator jaws.

FIG. 25a is a section view of clip magazine taken along line 25a-25a of FIG. 25.

FIG. 26 is a bottom plan view of clip magazine showing clips and clip advancing ladder within the magazine.

DETAILED DESCRIPTION OF PREFERRED EMBODIMENT

Figure 1:
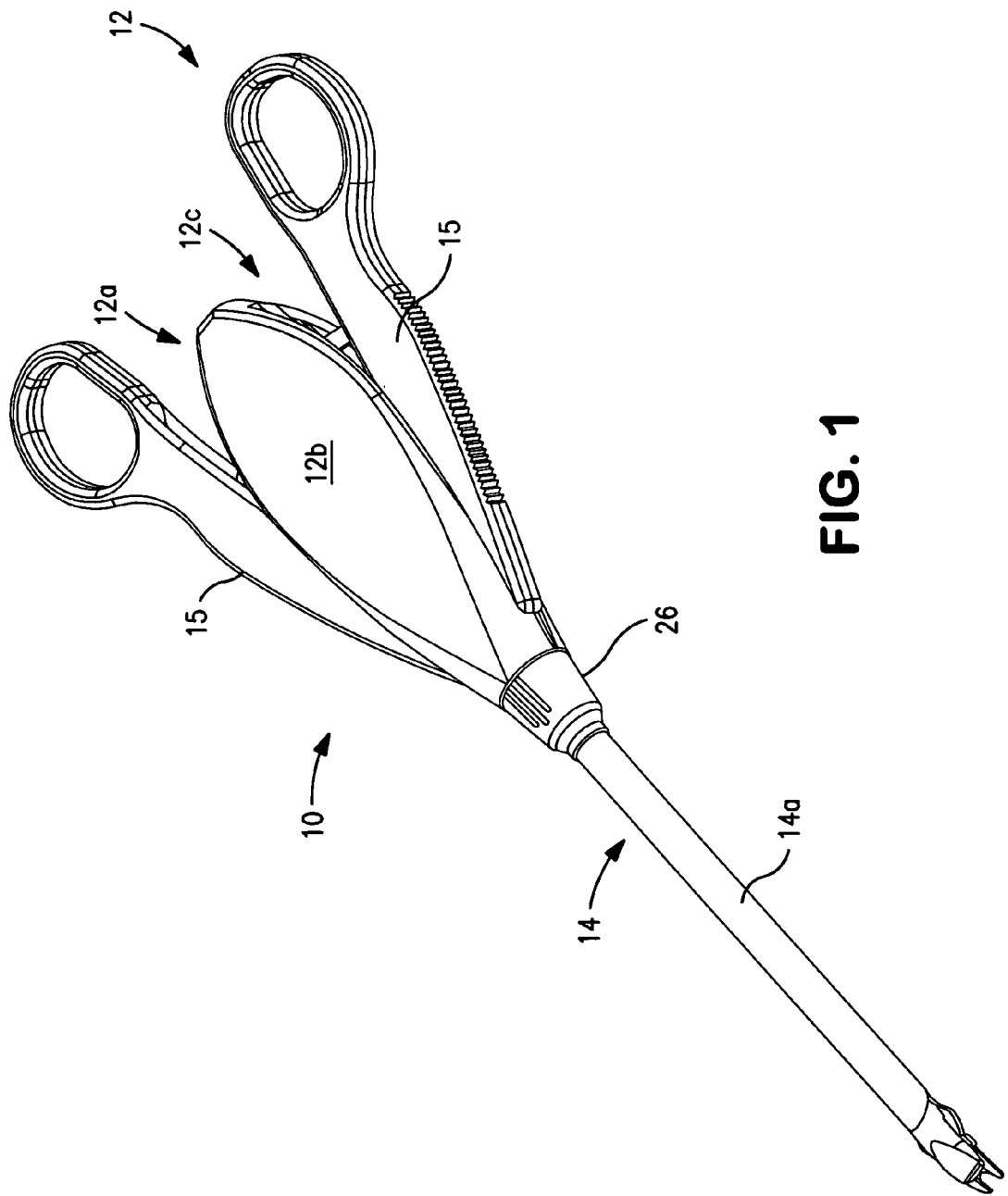
FIG. 1 is a perspective view of a preferred embodiment of surgical clip applicator comprising handle and cartridge according to the invention.

Referring to the drawing, a preferred embodiment of the surgical clip applier 10 comprises operating handle 12 and clip applicator cartridge 14.

The operating handle (FIGS. 1-3, 6a-b) is preferably scissors type with housing 12a of upper 12b and lower 12c shell members, scissor handles 15, cartridge socket 16, and an interior operating assembly of connecting links 18, linear actuator 20, scissor handle main spring 22, and anti-backup mechanism 24. Clip applicator cartridge 14 is inserted into the handle cartridge socket 16 for cooperation with handle interior assembly such that the handle provides the cartridge with linear reciprocating motion of fixed excursion controlled by anti-backup mechanism that restricts linear motion received by the cartridge to full close and full open or release strokes. The scissor handle main spring urges the linear actuator, scissor handles, and clip applicator cartridge including clip applying jaws to open position shown in FIGS. 1, 3, and 6a. The cartridge when assembled to the handle is held against rotation about the cartridge axis as described more fully below.

The clip applier cartridge end cap 26 shown in FIGS. 2, 13a-c, 14, and 15 provides interface for assembling cartridge and handle. The cap has a hollow cylindrical body 26a for receiving cartridge sleeve 14a and positioning T-end 28a of cartridge puller bar 28 for connection to handle. The cap further has locking lugs 26b extending radially from diametrically opposed points on the body, and a flared shroud 26c for gripping and rotating the cartridge as it is inserted into the handle cartridge socket 16.

Figure 2:
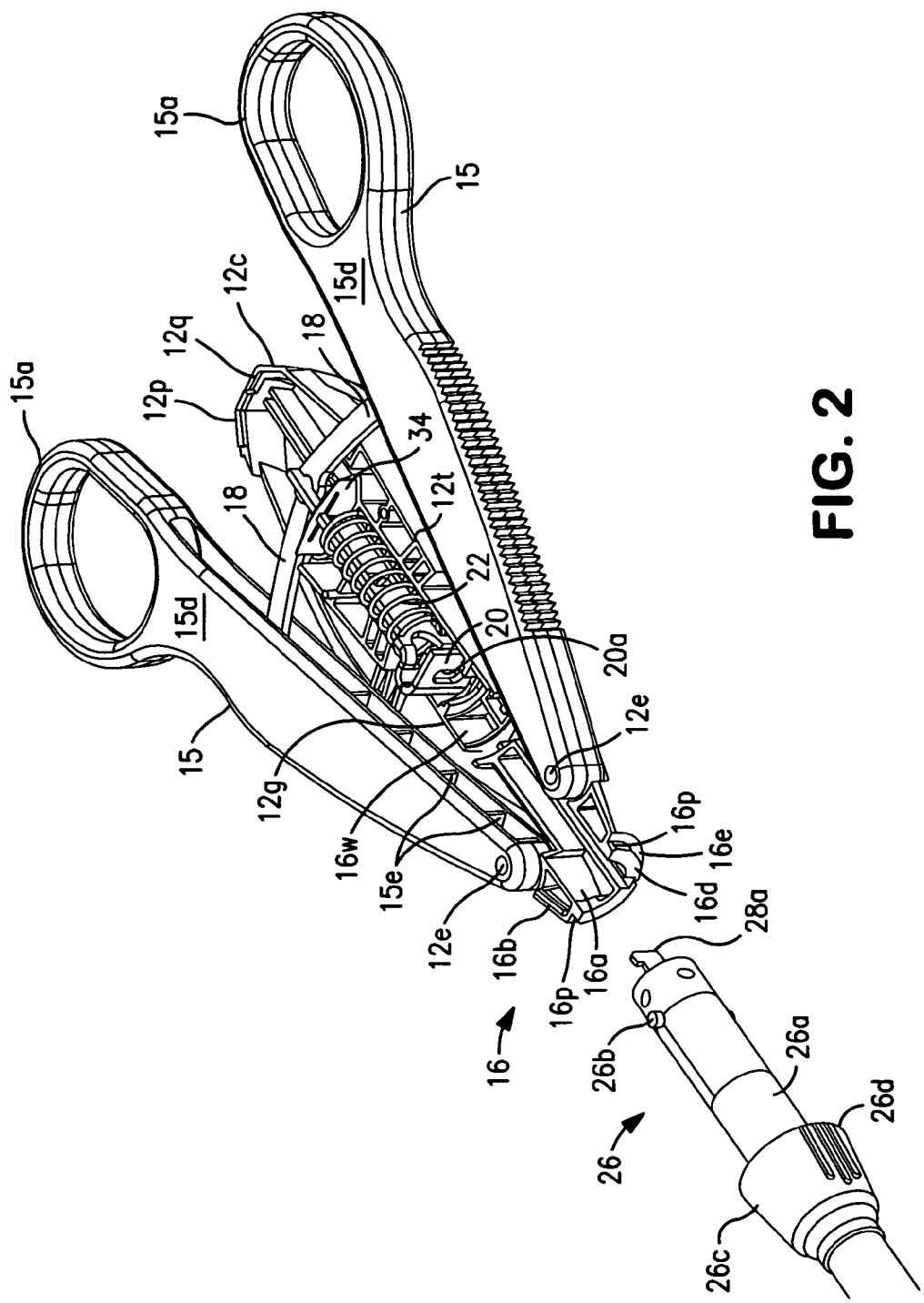
FIG. 2 is a perspective view of the surgical clip applicator of FIG. 1 with top cover shell of handle removed showing handle lever arms, handle socket for cartridge, subassembly of linear actuator, handle connecting links, handle main spring, and anti-backup mechanism; and further showing cartridge end cap.
Figure 3:
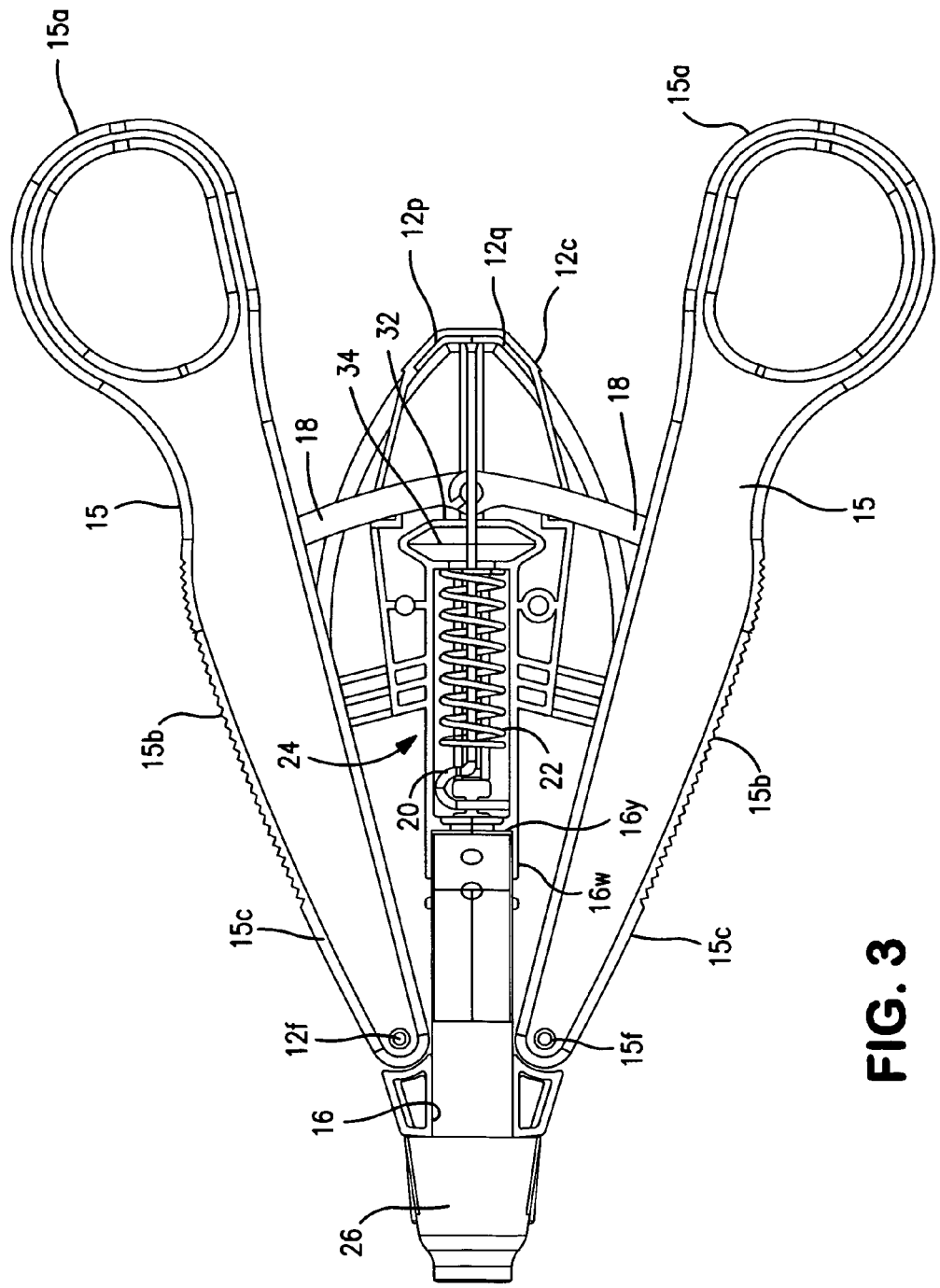
FIG. 3 is a plan view of handle of applicator of FIG. 1 with cover removed to illustrate general arrangement of linear actuator, handle connecting links, handle main spring, and anti-backup mechanism, together with cartridge end cap in place within the handle.
Figure 4:
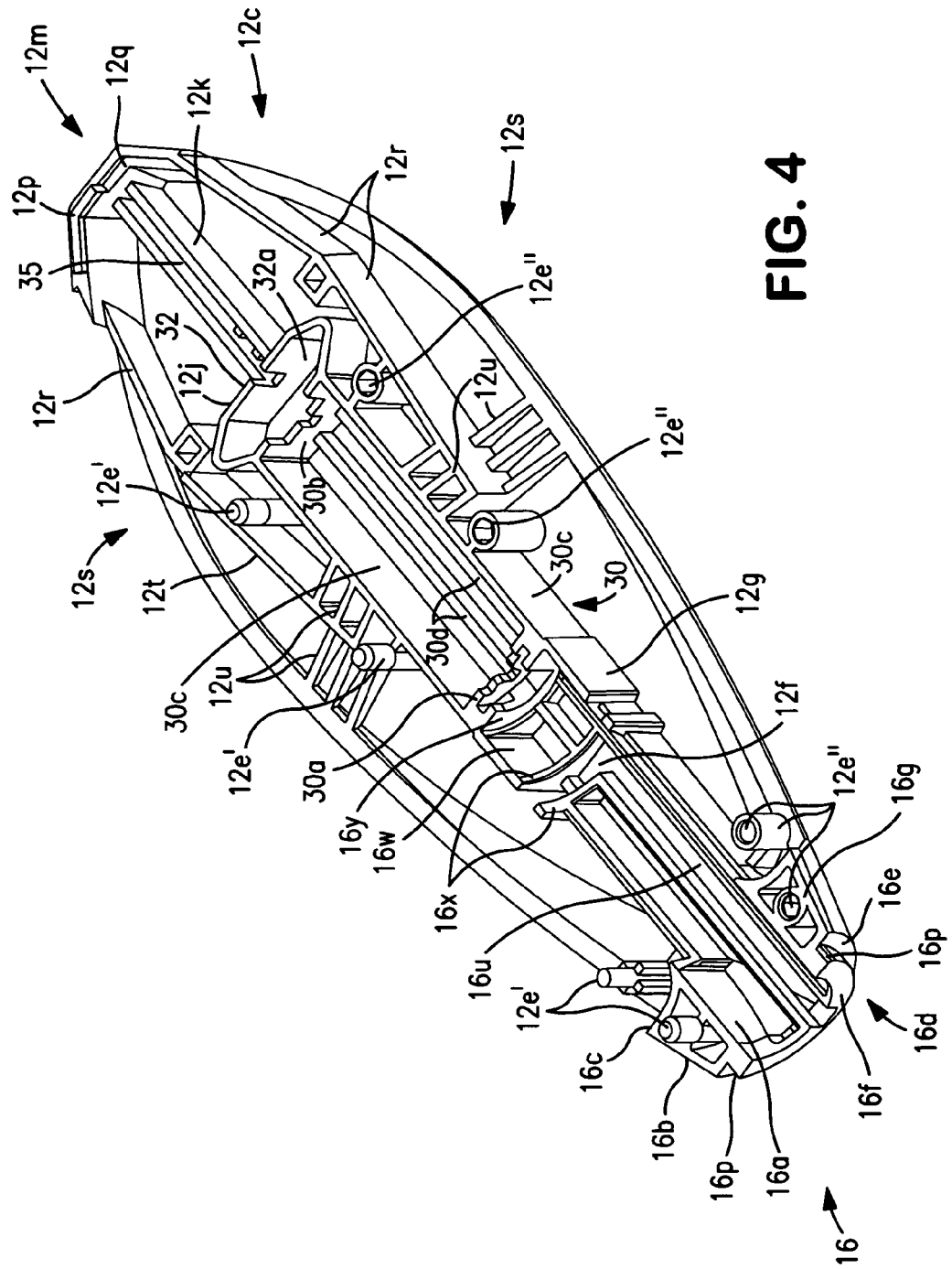
FIG. 4 is a perspective view of interior structure of handle cover shell showing cartridge socket, pivot posts, linear actuator housing and guide rails, aligned slots for positioning anti-backup spring, and guide channel for linear actuator.
Figure 5:
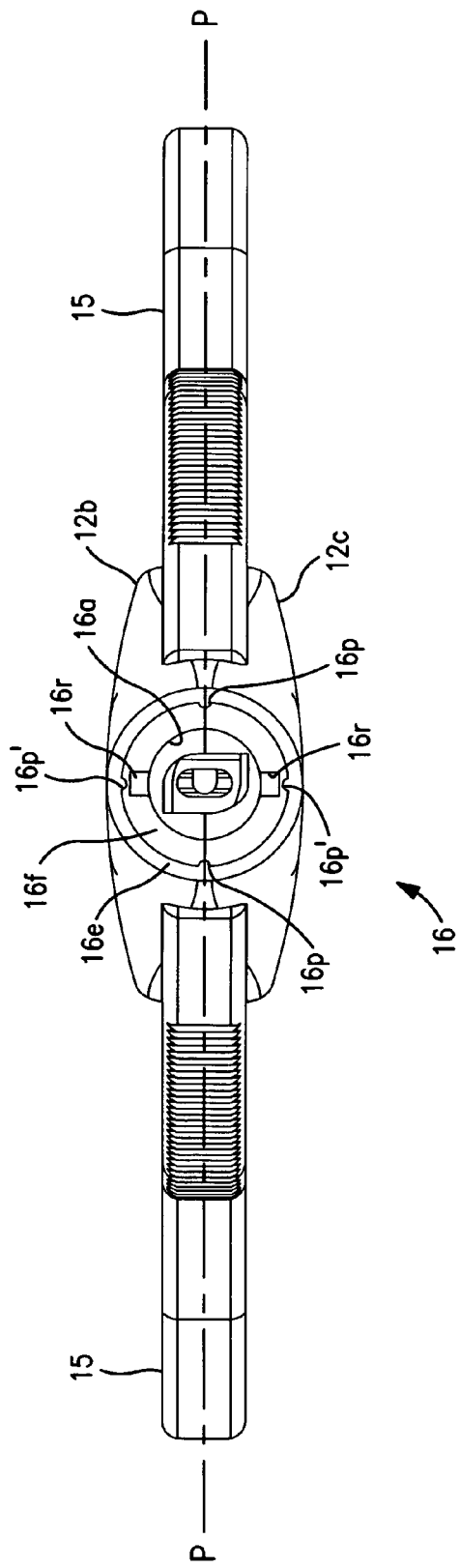
FIG. 5 is a front end elevation view of applicator handle of FIG. 1 showing cartridge entrance socket.

Referring to FIGS. 1-4, scissors handle 12 comprises housing of upper 12b and lower 12c shell members defining an interior space with pivot posts 12e for mounting handle lever arms, cartridge socket 16 for receiving and holding cartridge by its end cap 26, and for positioning an interior assembly of connecting links 18, linear actuator 20, handle main spring 22, and anti-backup mechanism 24. FIGS. 2-4 illustrate interior configuration of lower shell 12c member which is identical to the interior configuration of upper shell member 12b. Lower shell member configuration of FIG. 4 comprises one-half each of the structure of pivot posts 12e, cartridge socket 16, transverse slot 12f, cage 12g, linear actuator box 30, transverse compartment 12j, guide channel 12k, segmented back wall 12m that are all brought to full complement when joined to identical upper shell member along plane P (FIG. 5). So, for simplicity of manufacture and assembly of the shells into housing 12a, the shells are identical parts made from the same tooling.

The back end of the housing terminates in segmented back-wall 12m (FIGS. 2-4) extending partially along shell periphery for closing and securing shells to each other. Securing tabs 12p project from the top of one side of the back-wall, and notches 12q are formed into the top of the other side of the back-wall. The tabs and notches of mating shells are fastened together to secure the housing at this location.

Longitudinally extending interior walls 12r provide side surfaces to define side openings and marginal interior space 12s for handle lever arms 15, while wall top surfaces 12t of upper and lower shells meet in plane P to provide compressive strength to assembled shell housing.

Pivot posts 12e (FIGS. 2, 4) comprise complementary centering and receptor posts having the functions of (i) pivot posts for lever arms in assembled handle, and (ii) aligning upper and lower shell members during manufacturing assembly of handle. So, centering post 12e' is preferably of cruciform base surmounted by centering pin, and receptor post 12e" is preferably a cylindrical base with topside recess 12e''' for receiving 12e' centering pin. When handle shells are assembled, the pivot posts for lever arms each comprise mating centering and receptor posts.

Multiple pairs (four shown in FIG. 4) of centering pins and receptor recesses serve an additional function as crush pins 12e' and sockets 12e". The pins 12e' have cylindrical side walls that press fit into hexagonal receptor sockets 12e" so as to hold shell members together without need for sonic welding, glue, or fasteners.

As best shown in FIGS. 4 and 5, the housing upper 12b and lower 12c shells join to form cartridge socket 16 opening for insertion of cartridge into handle and an adjacent recess 16e for receiving the flared rim 26d of cartridge end cap. The socket opening 16 is broadly defined by cylindrical interior wall 16a, frusto-conical outer wall 16b, by transverse support ribs 16c between these walls, and by front wall 16d divided into recessed annular shoulder 16e and annular front face 16f. The socket opening further includes upper and lower rib and wall surfaces 16g where shells meet in plane P to form socket opening.

As noted above, the cartridge is connected to the handle by means of the cartridge end cap. As shown in FIGS. 2, 5 and 13a-c, socket front wall is provided with four exterior notches 16p and two entry openings 16r for receiving and retaining the cartridge by its end cap. A first set of notches 16p (FIGS. 2 and 5) result from mating bevels in front wall 16f, and a second set of notches 16p' are formed in the wall in vertical opposition as seen in FIG. 5. Front wall also has entry openings 16r aligned with notches 16p' which openings receive locking lugs 26b for guiding and holding the end cap in the cartridge socket. Cartridge cap lugs 26b and cartridge cap ribs 26e (FIG. 14) are also aligned for insertion of cartridge cap and cartridge into the handle.

As shown in FIGS. 2 and 5, the recessed surface 16e of upper and lower shells have mating bevelled surfaces 16p formed across seam that together define notches which register with ribs 26e (see FIGS. 13, 14) on the inner surface of cartridge cap shroud 26c. For assembly of end cap to socket, end cap ribs 26e register with notches 16p' and locking lugs register with entry openings 16r. After full insertion of cartridge cap into handle socket, the cartridge with its cap is rotated a quarter turn clockwise to final assembled position. The notches 16p and ribs 26e interlock in final assembly of cartridge and handle to restrain rotation of cartridge on its longitudinal axis. By this assembly arrangement, the cartridge remains in position fixed against rotation with respect to handle as shown in FIG. 1 and prevents undesirable changing of orientation of jaws with respect to the handle while a physician employs the clip applier in a surgical procedure.

As best shown in FIGS. 4 and 6a-b, cartridge socket 16 extends from cartridge opening at front end of the housing into the housing interior. Socket is defined by side panels 16s and by parallel guide ribs 16t defining an open ended channel 16u for receiving locking lugs 26b and guiding clip applier cartridge into position in the handle. Guide ribs at their inner end terminate at a transverse slot 12f situated between transverse walls 16x for receiving and retaining cartridge cap lugs. When cartridge is assembled to handle, lugs travel through guide ribs, and at the end of travel the cartridge is rotated one-quarter turn on its axis bringing lugs into final position within upper and lower transverse slots.

The inner reach of the cartridge socket includes a cage 16w defined by spaced side ribs 12g, circular inner ribs 16x, and by back wall 16y for receiving the end of cartridge shaft cap as its retaining lugs enter transverse slots as shown in FIGS. 3 and 4. The back wall defines a front face stop for cartridge assembly and also a back face stop for limiting excursion of linear actuator 20 in forward direction. In addition, the T-end 28a of cartridge puller bar projects through back wall for connection with linear actuator through aperture 20a. At this connection, linear reciprocating motion is transmitted from handle to cartridge.

The upper and lower housing shell inner surfaces further define a linear actuator box 30 comprising front 30a, rear 30b, and side 30c ribs for positioning the linear actuator 20 and handle main spring 22. Parallel axially extending rails 30d within the box support and center linear actuator 20 and main spring 22 within the handle. Handle main spring 22 is coiled about the linear actuator and is compressed (FIG. 6b) as handle lever arms 15 are closed. A transverse compartment 32 adjoins the back end of the box for positioning an anti-backup spring 34. The anti-backup spring 34 and linear actuator 20 form the anti-backup mechanism 24.

As best seen in FIGS. 4 and 6a-b transverse compartment its back wall 32a opens into guide channel 35 for receiving linear actuator along its edges for the purpose of guiding and constraining linear movement of the actuator during handle actuation.

The housing shell is further provided with additional interior strengthening ribs 12u.

As shown in FIGS. 1, 2, and 4, handle lever arms 15 are nested in side openings 12s of assembled shell housing, are mounted on pivot posts 12e for squeeze and release movement, have connecting links 18 for transforming squeeze and release movement into linear reciprocating movement received by linear actuator 20, are held in normal release position by main spring 22 urging linear actuator to position of FIGS. 2 and 6a, and have squeeze and release movement limited respectively by guide channel 35 and by back face stop 30a that limits forward excursion of linear actuator. In addition, squeeze and release movement of lever arms is further regulated by anti back-up mechanism 24 described below in detail.

The handle lever arms 15 are identical each having integral closed loop 15a for thumb and forefinger operation. Each lever arm is defined by a spine 15b extending from closed loop to pivot end 15c of the arm, by upper and lower parallel webs 15d extending inwardly from the spine, extending from closed loop to pivot end of the arm, and having strengthening ribs 15e in the space between webs. The pivot end 15c of each arm includes a bore 15f by which the arms are pivotally mounted to pivot posts 12e.

Upper and lower webs define a recess opening from web inner margins. The recess in each lever arm accommodates handle links (see FIGS. 6a-b, and 8-10) secured at one end within the recess by a pivot pin 18a. Each link is preferably arcuate with C-shape inner aperture 18b for pivoting connection to links post 20b at rear of linear actuator. In like manner, each link has hook shape outer aperture 18c for pivoting connection to a lever arm pivot pin 18a. As seen in FIGS. 6a-b, and 8-10, an inward or squeeze movement of handle lever arms causes links to move from release position of FIG. 6a to squeeze position of FIG. 6b while moving linear actuator 20 against return force of main spring 22. It is by this movement of the handle lever arms that linear reciprocating motion is developed for actuating internal components of clip applicator as recited more particularly below.

Each of the connecting links 18 is pivotally connected to an end of linear actuator 20 seen in FIGS. 8, 9, and 10. The linear actuator (FIGS. 7a-d, 9-11) comprises elongate main body bar 20c with integral head plate 20d. The linear actuator has handle links post 20b defined by recesses 20b' in the body bar. Links post receives C-shaped apertures 18b of each connecting link by which squeeze of handles produces linear movement of actuator. Linear actuator shoulders 20e are formed at junction with of body bar with head plate for application of main spring thrust to linear actuator.

The handle main spring 22 is a compression spring coiled about body bar with spring front edge abutting shoulder, and spring rear edge abutting rear wall 30b (FIG. 4) of linear actuator box. As shown in FIG. 6b the spring compresses between shoulders 20e and wall 30b for handle squeeze, and develops and exerts spring force against the shoulder urging linear actuator and handle lever arms 15 to normal release position.

Linear actuator head plate includes transverse section with internal aperture 20a for engaging cartridge pull bar 28a (FIG. 3) whereby cartridge receives linear reciprocating motion for operating cartridge components as fully described below. The linear actuator illustrated in FIGS. 7a-d and 9-11 further comprises an anti-backup mechanism 24 cooperating with anti-backup spring 34 (FIG. 12). Actuator body spaced slots 20f-g, preferably rectangular in form, accommodate flexing action and toggling over of spring tabs 34a of anti-backup spring. The slots also mark limits of linear travel of the actuator when moved by lever arms and connecting links. The linear actuator body bar surface 20h between slots may be coarsened as by knurling to increase surface friction to serve as an anti-backup surface for an anti-backup spring. Coarsening assures that spring tabs maintain contact with linear actuator, and knurling allows for incremental detenting that provides a clicking sound to the instrument while the linear actuator is in motion.

The anti-backup spring 34 comprises a plate 34b of spring steel with an H-shape slot 34c defining cooperating spring tabs 34a separated by center gap 34d with the tabs flexing forward and back with respect to spring heads 34e situated at opposite ends of spring plate.

When linear actuator and anti-backup spring are assembled (FIGS. 9, 10) spring center gap 34d and tab margins 34a' reside in linear actuator rear slot 20g with tab margins passing into the slot. The center gap 34d provides an interference passage between confronting tab margins permitting the linear actuator bar to pass through with tab margins dragging along coarsened bar surface. When handles and levers generate rearward linear movement of actuator, actuator bar moves through the slot and the tab edges drag along bar surface. In this dragging configuration, the tab edges prevent the linear actuator moving in opposite, i.e., forward direction. If a surgeon releases the handles with tab edges in dragging configuration, handle main spring will not return handles to release position. So, it is necessary to resume rearward dragging movement of tab edges over bar surface until tab edges arrive at linear actuator forward slot 20f where they release coarsened surface and are able to toggle over so as to permit movement of linear actuator under influence of main spring in forward direction.

The anti-backup spring further comprises body bar recesses 34f on opposite sides of center gap 34d which conform to and accommodate body bar margins as best shown in FIG. 2. Recesses 34f hold the spring square to the linear actuator body bar through the full range of actuator/spring cooperation without warping or distortion of the spring body.

T-shape end 28a of cartridge puller bar fits into and is retained by aperture 20a in linear actuator head plate. As described above when the cartridge is assembled to handle and rotated one-quarter turn, the T-end of the puller bar is captured by linear actuator, entering in a vertical orientation and moving a one-quarter turn to horizontal.

Handle assembly is shown in FIGS. 2, 3, and 6a-b and includes placement of linear actuator, with coiled main spring, and placement of anti-backup spring in transverse slot. Handles are placed in position with end bores on pivot posts and C-shape link apertures mounted at linear actuator post. The housing shells are then assembled closing in the handle assembly.

FIGS. 2, 3, and 6a also show the position of the anti-backup mechanism with handle lever arms in release position and with rear slot of the anti-backup bar adjacent the anti-backup spring. In FIG. 6b, the anti-backup bar has passed fully through spring space at squeeze position of handle lever arms. The spring tabs have entered bar slot so that the tabs can "toggle over". With release of the handles the compressed main spring urges the linear actuator to return to the open position of FIG. 2. The return force of main spring is sufficient to push linear actuator to release position while overcoming frictional drag anti-backup spring tabs along coarsened bar surface.

FIG. 3 also illustrates the clip cartridge assembled to the handle with the T-end of the puller bar held by its cage on the linear actuator.

Referring now to FIGS. 16-20, clip cartridge 14 components comprise end cap 26, cartridge sleeve 40, cartridge chassis 42, cartridge cover 44, and cartridge interior operating components 46.

Cartridge end cap 26 shown in FIGS. 13-15 as part of the clip cartridge assembly provides the means for interconnecting the cartridge to the handle. End cap comprises tubular body 26a with cylindrical axial cavity 26f for receiving cartridge sleeve 40 in nested relation. A pair of positioning lugs or posts 26b project radially outward from opposite sides of body along an axis E-E' (FIG. 16) which lies in the same plane as the puller bar 28. This co-planar arrangement orients the T-end 28a of the puller bar into necessary position for connection to handle linear actuator. When the end cap is assembled with the clip applier handle, positioning lugs enter channels 16u situated on the interior of upper and lower housing members, guide T-end toward and into slotted end wall of puller bar cage 16w. The shaft cap is then rotated one-quarter turn clockwise for capturing the T-end within the cage and the positioning lugs within transverse slots 12f provided in handle housing interior walls. It is by this connection that clip cartridge is held fast to the handle and that the handle transmits linear motion to the cartridge.

Figure 20:
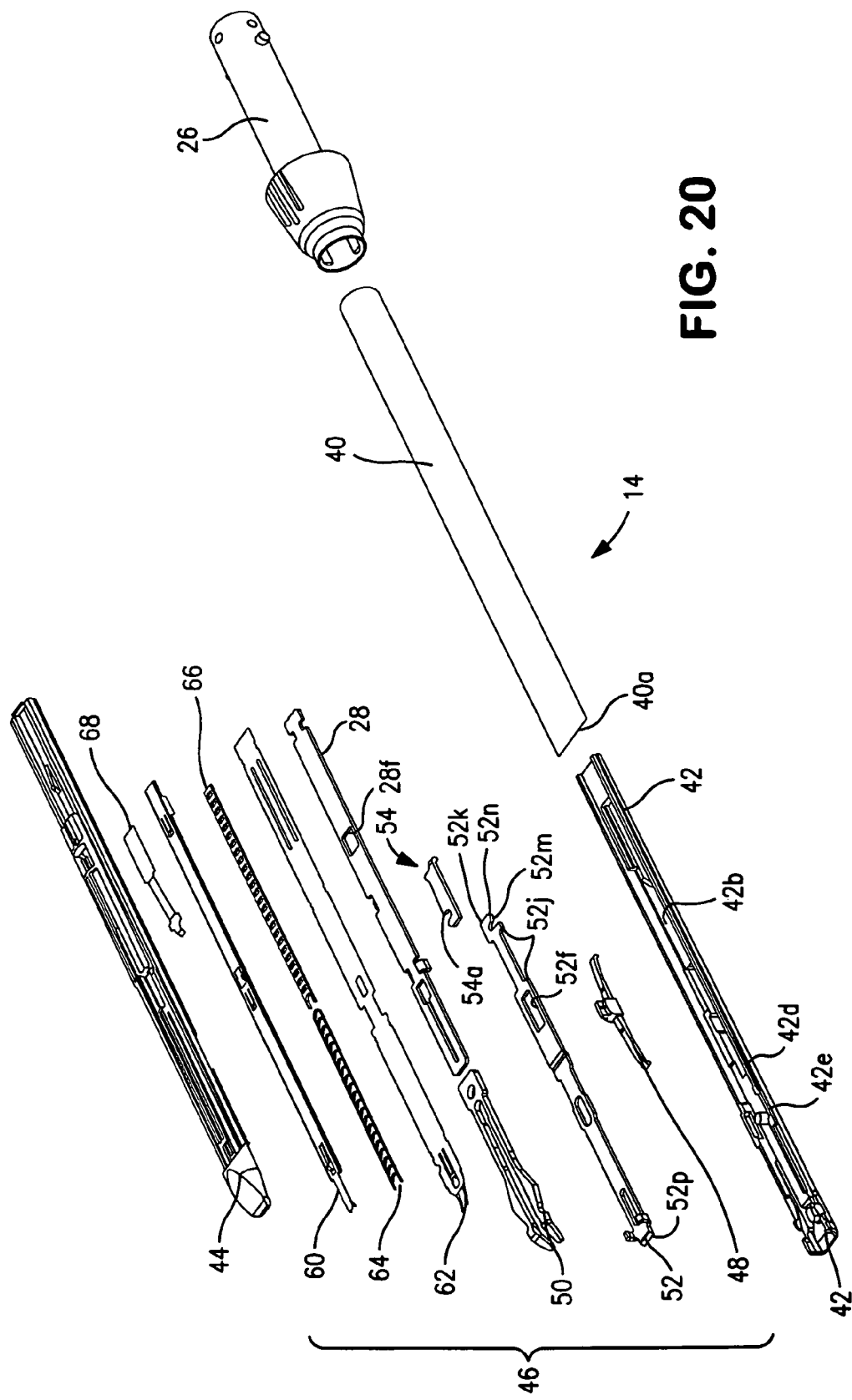
FIG. 20 is a perspective view layout of full complement of cartridge internal components including sleeve, chassis, cover, and first and second sets of cartridge members.

FIG. 20 illustrates cartridge sleeve 40, cartridge chassis 42, cartridge cover 44, and cartridge interior operating components 46 in relative positions prior to being assembled into a functioning clip cartridge.

The sleeve is an elongate, preferably stainless steel, open-ended tube with bevelled front end 40a for abutment with hips 42a, 44a on cartridge chassis and cartridge cover shown in FIGS. 16-19.

Cartridge chassis 42 forms a stationary base with longitudinal channel 42b defined by base panel with lock out recess 42c, upright side walls 42d marginal edge notches 42e that fit corresponding cover edges 44c (FIG. 25), jaw post 42f, a front end opening 42g for clip applier jaws 50, a cam bar guide post 42h, a toggle cam surface 42k, and a T-bar rear end opening 42m and support ledge 42n.

The lock out recess 42c (FIG. 19) opens through the base and has spaced ledges 42o including ledge panels 42p and ledge end walls 42q for supporting lock out block 48.

The jaw end of the cartridge chassis is configured for mounting clip applying jaws in normally open, position allowing for the jaws to be cammed closed for applying surgical clip. Chassis sidewalls are recessed 42r just aft of the front end opening for accommodating jaw apexes 50a with jaws in open position. As jaws open and close in operation, jaw apexes move in and out of sidewall recesses. The chassis base near its front end has an upstanding oblong guide 42f with rounded ends that serves dual functions of jaw post and guiding cam bar as it reciprocates in operation. Accordingly, cam bar has oblong slot 52a for jaw post 42f.

Figure 21:
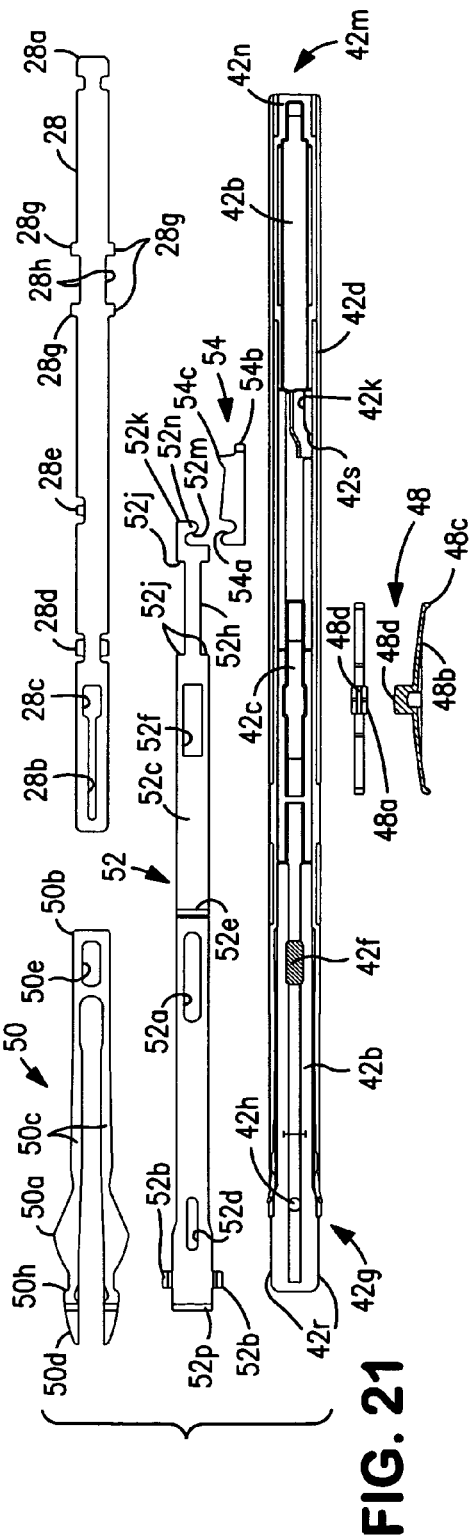
FIG. 21 is a plan view of a layout of first set of cartridge members that actuate clip applicator jaws.

Components for actuation of the jaws and for locking the clip applier against actuation after the last clip is used, are mounted in stacked relation within the cartridge chassis as shown in FIGS. 20 and 21. These components are jaws 50, jaws cam-bar 52, cam-bar safety toggle 54, puller bar 28, and lock out 48. Lock out comprises a central lug 48a with legs 48b of equal length extending away from the lug and terminating in downwardly depending tips 48c. The combined length of the legs from tip to tip is approximately equal to the length between ends of ledges 42o (FIG. 19) in chassis recess. The lock out fits into chassis recess with legs extending along the recess and with leg tips resting on ledges and abutting recess end walls. In this position, the legs provide spring action for the central lug so as to give biased flexing support wherein the lug is urged upward from chassis base panel to normal position, and the lug is readily pushed down against leg spring action. The chassis base panel is open through the recess to accommodate the lock out in downward position until the last clip is used whereupon the lock out is released for upward movement as more fully described below.

Figure 22:
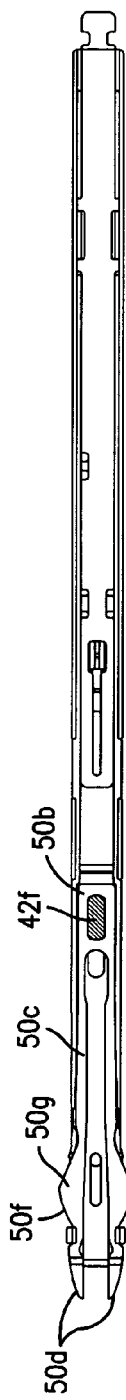
FIG. 22 is a plan view of an assembly of first set of cartridge members of FIG. 21 showing jaws in open position, i.e., with pull bar in forward position.

Jaws 50 shown in FIGS. 20-22, comprise base plate 50b with jaw spring arms 50c extending in parallel from the base terminating in cooperating jaw heads 50d. The base plate has an opening 50e for securing the jaws to jaw post 42f of the cartridge chassis. The outer surfaces of each spring arm have cam surfaces 50f defined by triangular enlargements 50g extending along each arm behind its jaw head. A notch 50h intervenes between the rear surface of each jaw head and the beginning of each enlargement. So, cam surface 50f lies between the notch 50h and apex 50a of each jaw arm triangular enlargement for cooperation with cam-bar 52 that opens and closes the jaws by engaging cam surfaces with cam fingers 52b. The jaws have a natural spring bias to open position and are forced closed by cam-bar fingers for crimping a clip in surgery. Jaws 50 overlie cam bar 52 that receives linear reciprocating motion from cartridge puller bar 28 wherein cam bar fingers open and close jaws as part of operating sequence of cartridge components.

Jaws cam bar 52 shown in FIGS. 20-22 for opening and closing the jaws comprises an elongate strip body 52c with oblong slot 52a fitting over chassis guide 42f; an oblong post slot 52d with rounded ends for accommodating chassis jaw post 42h by which jaws are secured to the chassis; a mid-way transverse shoulder 52e for shifting position of rear portion of the cam-bar to pass over the lock out; an oblong lock out slot 52f; a necked-down section 52g defined by recessed side edges 52h extending between shoulders 52j by which the cam-bar receives reciprocating motion from the cartridge puller bar 28; and a toggle block 52k having interior sinuous toggle surface 52m for engagement and cooperation with cam-bar safety toggle 54.

The cam-bar safety toggle 54 shown in FIGS. 20, 21, 23, 24, is an elongate plate having an exterior sinuous toggle surface meshed with cam-bar interior sinuous toggle surface 54a for rotation about pivot point 52n as the cam-bar is pulled by the puller bar 28 in clip applier operation. The safety toggle further has a dependent tang 54b guided in pivoting motion by a shoulder or salient 42s extending laterally within chassis cam surface 42k for engagement by puller bar tang 54b. The safety toggle is effective to nudge cam bar 52 forward after a clip is applied in surgery. This nudging action prevents that condition where jaw cam surfaces 50f and cam bar fingers 52b adhere to each other and fail to separate after the jaws apply a clip. The nudging mechanism occurs when applier handles are released and puller bar returns to release position, puller bar tang 54b riding within cam surface 42k strikes safety toggle shoulder 42s pushing the safety toggle forward and downward thereby moving cam bar fingers forward along jaw arm cam surfaces to cam notches 50h permitting the jaws to spring open as desired.

The cam bar front end defines a tissue fence 52p to prevent tissue extending inward into jaws and pushing a clip backwards in the jaws as the applier is used in surgery.

Cartridge puller bar 28 comprises an elongate plate through which reciprocating motion developed by the clip applier handle is received by the cartridge and distributed to cartridge operating components both clip crimping jaws and surgical clip feeding mechanism by which clips are fed one by one into the clip crimping jaws for each cycle of the clip applier. The puller bar includes narrow 28b and wide 28c lock out slots for respectively accommodating upper tip 48d of the lock out in narrow slot 28b as the puller bar reciprocates over the lock out in normal operation, and accommodating the lock out body in wide slot 28c as it rises to lock the clip applier from further operation after the last clip has been used in surgery. The puller bar further includes depending tangs 28d cooperating with cam-bar recesses for moving the cam bar side by engaging edge recesses 52h in order to close the jaws in applying a clip in surgery; a toggle tang 28e cooperating with cam bar safety toggle shoulder 54c for a purpose detailed below; rectangular opening 28f (FIG. 20) for receiving magazine tangs through which the puller bar delivers reciprocating motion to the clip magazine components as more fully described below; and T-bar 28a connection to handle as described above. Rectangular opening 28f is a preferred embodiment of means for delivering linear motion to magazine tangs, and another preferred embodiment being spaced puller bar shoulders 28g (FIG. 21) marking edges 28h that nest with magazine tangs to transmit linear motion.

Figure 23:
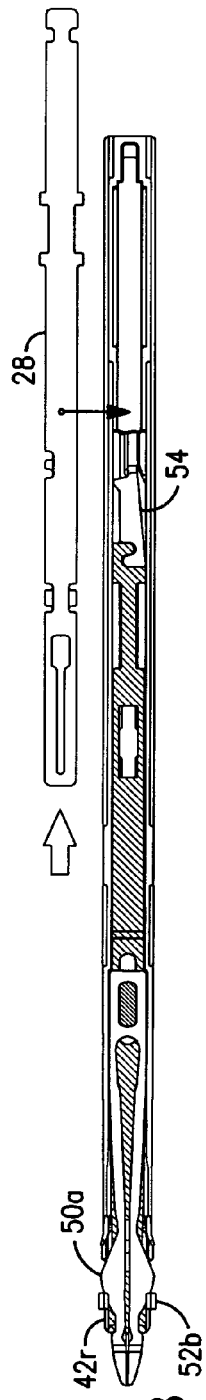
FIG. 23 is a plan view of an assembly of first set cartridge members of FIG. 21 showing jaws in closed position with pull bar in rear position and with pull bar placed alongside assembly to illustrate inner members of the set.
Figure 24:
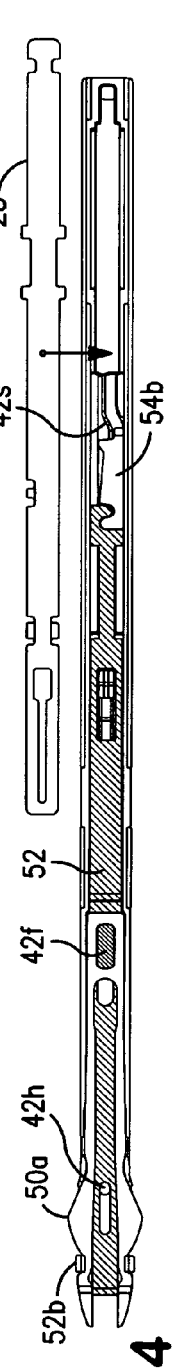
FIG. 24 is a plan view of an assembly of first set cartridge members of FIG. 21 showing jaws in open position with pull bar in forward position and with pull bar placed alongside assembly to illustrate inner members of the set.

Referring to FIGS. 20-24, jaws 50 are secured to chassis 42 at jaw post 42f, and except for opening and closing, the jaws are stationary with respect to the chassis. Lock out 48 remains within its recess 42c with its upwardly projecting block being accommodated by cam bar opening 52f and puller bar wide 28c and narrow 28b slots which pass over the lock out in normal operation of the clip applier. Cam bar lies between chassis and jaws with jaw post 42h passing through slot 52d, and chassis guide post 42f riding in cam bar guide slot 52a. Puller bar overlies cam bar and its safety toggle 54 with puller bar lock out slots 28b-c aligned with lockout block, tangs 28d in registry with cam bar recesses 52h, and toggle tang 54b forward of toggle salient 42s (FIG. 24).

Cam bar side edge recesses 52H cooperate with puller bar tangs 28d to create a hiatus in movement of jaws from position of FIG. 24 to that of FIG. 23. The hiatus is an interval of jaws remaining open as a clip arrives and is being inserted into the jaws by clip handling mechanisms described in detail below.

A clip is crimped by the handle moving puller bar to the position of FIG. 23. As this motion is occurring, puller bar tangs 28d engage cam bar rear shoulders 52j moving cam bar to the rear with cam bar jaw tangs 52b riding along cam surfaces 50f and closing the jaws. At the same time, cam bar safety toggle 54 pivots counterclockwise (compare FIGS. 24 and 23) to locate shoulder 54c in the return path of puller bar tang 28e. The safety toggle is constrained to pivot about meshing sinuous surfaces as its tang 54b rides in chassis cam track 42k to canted position of FIG. 23.

When the handle is released handle main spring urges puller bar 28 forward so that its tang 28e strikes shoulder 54c moving safety toggle 54 and cam bar 52 forward to the position of FIG. 24. Safety toggle tang rides down the chassis track 42k to normal position. Puller bar tang 28e comes to rest well forward of shoulder 54c in position for subsequent applicator cycle. Puller bar magazine slot 28f delivers reciprocating motion to cartridge components now to be described for delivering clips one-by-one to the applicator jaws.

Components for holding and feeding surgical clips one at a time to the applicator jaws are mounted in stacked relation within the cartridge. These components are clip magazine 60, magazine floor plate 62, clip stack 64, clip advancing ladder 66, cover detent spring 68, and cartridge cover 44 as best seen in articulated positions in FIGS. 20 and 25. The cover detent spring 68 is mounted at a recess in the underside of cover 44 so that spring 68 is stationary with respect to cyclical movements of clip magazine as described in detail below.

Clip magazine 60 is a C-shaped channel with main panel 60a, depending side panels 60b, and in-turned marginal flanges 60c defining a cartridge chamber or space for receiving and containing clip stack 64 aligned with clip advancing ladder 66. The marginal in-turned flanges retain clips and ladder within cartridge chamber. Clip magazine drive tangs 60d extend from marginal flanges and pass through floor plate slit for engagement with puller bar drive slot 28f or drive edges 28h. The tangs are point of reception of reciprocating motion employed to actuate clip holding and feeding components. So, for each cycle of pull and return strokes of the clip applier handles, puller bar drives clip magazine with clip stack and clip advancing ladder through full reciprocating excursion generated by puller bar. Tangs and floor plate slits are dimensioned to accommodate full reciprocating excursion of clip magazine and puller bar.

The clip stack 64 comprises a line of clips C with clip tips Ca engaging shoulders Cs of clip next ahead. In a clip stack successive clips engage each other in a clip tips-to-clip shoulders manner. Accordingly, a clip increment Ci (FIG. 26) may be defined as the distance measured on a given clip between its tips and the point on the given clip's shoulders that is engaged by the tips of the next successive clip. The clips are confined within the clip chamber 60h defined by magazine in-turned flanges 60c, clip magazine flanges 60b and main panel 60a. Clip advancing ladder 66 is situated within the clip chamber in longitudinal alignment with the clip stack, and during operation of the clip applier moves in unison with the clip stack. As more fully detailed below in reference to clip applier operating cycle, the stack and ladder along with the magazine move toward and move away from the applier jaws. The clip advancing ladder comprises longitudinal, parallel beams 66*a* with a series of parallel rungs 66*b* extending athwart the beams, with the rungs spaced a clip increment apart. An opening exists in each space defined by beams and rungs for engagement with magazine detent springs 60*f-g*. The magazine detent springs each engage a ladder opening and hold the ladder and stack within magazine clip chamber as the full ensemble of magazine with detent springs, clips and ladder move toward the jaws. On return movement of the full ensemble, the magazine detent springs slide past a single rung as the ladder is restrained by stationary cover detent spring 68. The ladder may have recesses instead of openings between rungs.

Clip magazine further comprises three leaf springs formed in main panel including claw spring 60*e* for clawing back the clip stack on the pull stroke of the handle that provides return travel of the clip magazine; and cooperating detent springs 60*f* and 60*g* that engage clip advancing ladder rungs and move the ladder and stack toward the jaws on return stroke of the handle. For a portion of return travel of the clip magazine the cover detent spring 68 restrains movement of the ladder and clip stack so that magazine detent springs 60*f-g* ratchet over a rung and come to rest in a rung opening or recess closer to the end of the ladder. So for a ladder rung pitch equal to a clip increment, the claw back spring 60*e* moves stack back, cover detent spring 68 holds ladder, and on forward magazine movement the ladder and stack move so as to net one clip increment forward movement for each pull and return cycle of the applier handle.

Clip magazine 60 further comprises rectangular slot 60*p* having dual functions, first, allowing cover detent spring 68 to extend through magazine panel to engage and restrain clip advancing ladder 66 against rearward movement as the clip magazine is being returned by the puller bar, and second, as an opening for entry of lock out spring block 48 to inhibit cartridge movement after last clip is used in surgery. Normally, slot 60*d* is closed over by clip advancing ladder 66 as the ladder advances clip stack toward the jaws one at a time for each cycle of the clip applier. The trailing end 66*c* of the ladder moves past lock out slot 60*d* after the last clip is moved into the jaws, whereupon the lock out 48, being spring biased, rises and its central lug 48*a* enters and remains in the slot 60*d*. The central lug also enters the puller bar lockout slot 28*c* to prevent further operation of the appliance. That is, movements of clip ladder and puller bar are physically and permanently blocked, handles can no longer be actuated, and the clip applier is empty of clips and can no longer be used.

The clip magazine 60 further comprises clip arm 60*j* and clip head 60*k* projecting from the front end of main panel 60*a* for engaging a lead clip by its shoulder and pushing it into the jaws on each return stroke of applier handles.

Figure 27:
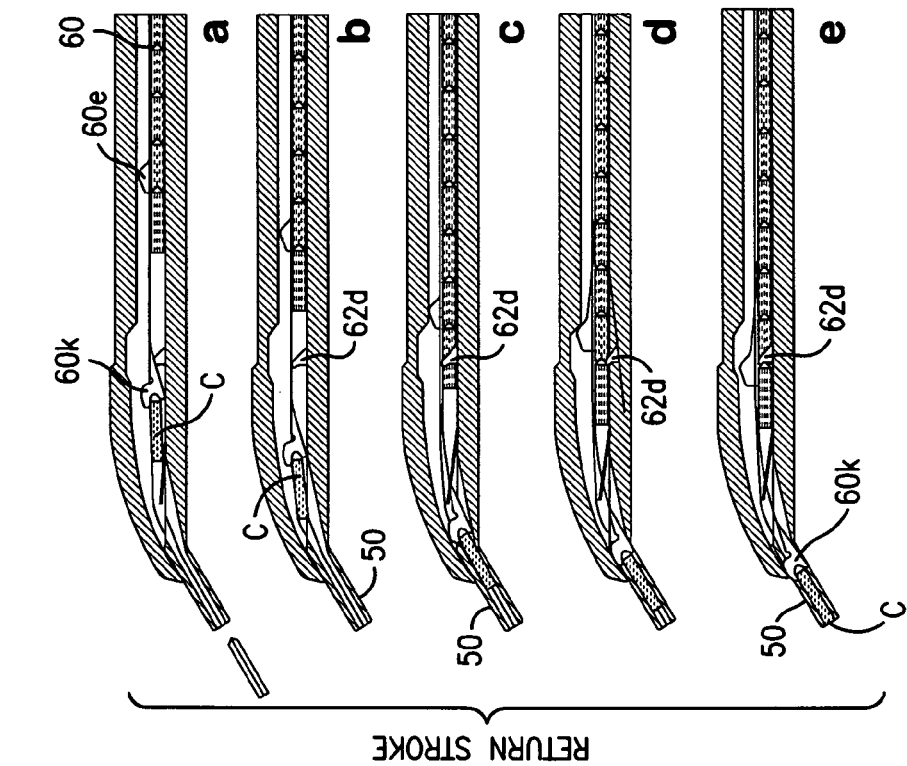
FIGS. 27a-e are section views of second set of cartridge members of FIG. 25 during pull stroke of the cartridge pull bar.

Magazine floor plate 62 is mounted along the length of cartridge cover 44 enclosing clip cartridge with clips and ladder within interior cover channel 44*c* (FIGS. 26,27). Both cartridge cover and magazine floor plate are stationary during clip applier operation. Floor plate 62 is an elongate strip having parallel slits 62*a* through which clip magazine drive tangs 60*d* pass for driving engagement with puller bar rectangular opening 28*f* (FIG. 20) or edge recesses 28*h* (FIG. 21) whereby puller bar delivers reciprocating motion to the clip magazine 60 and its ladder and clip stack components; a lock out slot 62*b* accommodating the lock out as it rises to lock the clip applier from further operation after the last clip has been used in surgery; edge recesses 62*c* engaging corresponding ridges on the cartridge cover for the purpose of holding the floor plate stationary to the cover against longitudinal movement; a clip capture spring 62*d* for separating a lead clip from the clip magazine preparatory to being moved into clip applying jaws; and front end ramps 62*e* for guiding a lead clip as it is being pushed into the jaws.

The cartridge cover is secured to the chassis and together with the chassis encases cartridge operating components. In addition, the cartridge cover cooperates with cartridge operation in the following aspects.

The cartridge cover holds cover detent spring 68 in fixed longitudinal position above clip stack and clip advancing ladder, and provides cover recess to accommodate spring flexing. Spring 68 comprises base panel 68*a* by which it is mounted to cover 44, and an inclined spring arm 68*b* to orient spring head 68*c* toward magazine slot 60*d*. The leading edge 68*d* of the spring enters magazine slot as the magazine undergoes rearward movement on pull stroke of the handle. Spring edge 68*d* engages a ladder opening and stops further movement of the ladder. The dwell of cover spring edge in magazine slot is regulated by magazine cams 60*m* fitted to main panel along each side of the slot. As the magazine is in rearward movement, cams 60*m* engage wings 68*e* of cover detent spring and lift the spring edge 68*d* out of magazine slot. Dwell of spring edge in slot is determined by distance between leading edge of the spring and front edge 68*f* of wings, such distance being selected to equal one clip increment. The ladder and line of clips therefore slip one clip increment with respect to the clip magazine as spring leading edge 68*d* engages a rung and stops ladder movement for each cycle of instrument handles. While the stack and ladder are restrained by the cover spring, magazine detent springs 60*f* and 60*g* slide over stack and ladder and the operative spring (determined by remaining length of stack and ladder) slides over the ladder coming to rest in an opening closer to the rear of the ladder.

The cover adjacent the jaws end of the instrument has an inwardly directed recess 44*d* and shoulder 44*f* for accommodating the magazine claw back spring 60*e*. As the magazine 60 undergoes return movement, the claw spring head 60*e* is depressed by both shoulder 44*f* and cover channel surface 44*c* into engagement with clip stack to claw back the stack with, return movement of the magazine.

Figure 28:
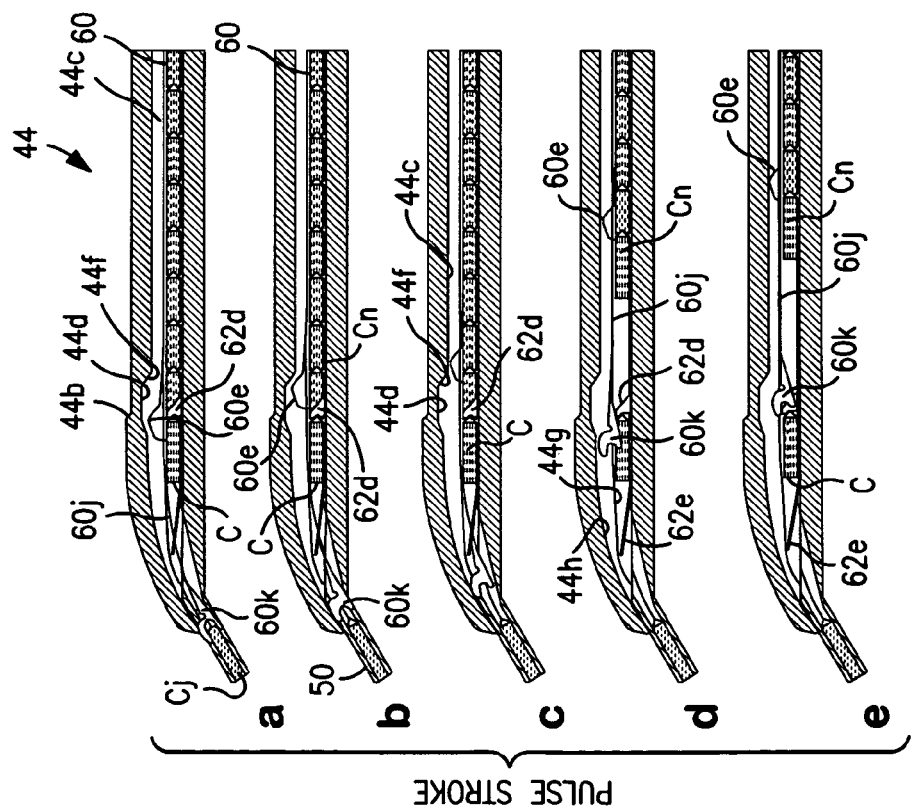
FIGS. 28a-e are section views of second set of cartridge members of FIG. 25 during return stroke of the cartridge pull bar.

As seen in FIGS. 27 and 28, cover 44 adjacent the jaws end of the instrument further comprises interior clip guide surface 44*g* and clip head recess 44*h* for guiding clips as they are pushed by magazine arm 60*j* and clip head 60*k* into applier jaws.

Referring to FIGS. 27 and 28, the clip applier cycle comprises a pull stroke and release stroke of the handle.

At start of the pull stroke magazine floor plate capture spring 62*d* has moved into position behind lead clip C to hold it there for duration of the pull stroke. The components for moving clips are in forward position with clip positioned in jaws (FIG. 27*a*). As pull begins and continues, clip magazine being pulled back by the puller bar retreats from forward position, clip arm 60*j* and clip head 60*k* withdraw from jawed clip $C_j$, and pass between stationary floor plate ramps 62*e*. Claw back spring 60*e* engages cover cam surface 44*f* and moves downward to grasp next clip $C_n$ and pull line of clips backward. At the end of the pull stroke, clip head 60*k* rides over the captured clip C coming to a stop behind the clip's shoulder in preparation for pushing the clip on release stroke of the handle.

As the clip magazine moves to the rear on pull stroke, the cover detent spring 68 finds and enters main panel opening 60*d* and restrains ladder movement so that the clip stack being drawn back by the claw spring closes up the space existing between stack and ladder. The cover detent is then lifted out of panel opening by main panel cams 60m. The dwell of cover spring edge in magazine slot is regulated by cams, fitted along side the slot which engage wings of cover spring and lift the spring out of magazine slot. Dwell is determined by distance between leading edge and front edges of wings, such distance being selected to, equal one clip increment. The ladder and line of clips therefore slip one clip increment along the clip magazine for each cycle of instrument handles.

On the return stroke of the applier handle, the clip head 60k pushes captured clip over floor plate ramps 62e and beneath cover guide surface 44g into open jaws.

The operational sequence of the clip applier cartridge as from its beginning status is as follows.
1. All moving components are in the forward or distal position.
2. A clip is in place within the open jaws and in contact with the forward tip of the magazine clip head pusher, an integral feature of the reciprocating magazine.
3. The second clip is in position within the magazine, forward of the detent spring, an integral feature of the floor, the purpose of which is to retain the second clip in place when the magazine moves rearward.
4. The remaining stack of clips extends rearward within the magazine and is in contact with the second clip at front and the advancing ladder at the rear.
5. The clawback spring in the forward portion of the magazine is in the upward, disengaged position.
6. The advancing ladder is movably contained in the magazine and moved forward to contact the stack of clips. It retains its position by means of a magazine ratcheting pawl (or spring) that allows the ladder to move forward while preventing backward movement. The pawl is an integral feature of the magazine and is engaged and relaxed.
7. The detent spring (ladder advancer), mounted stationary on the cartridge cover is in disengaged free sliding contact with the top flat surface of the magazine.
8. Downward tabs located at the rear of the magazine project through the floor to engage the puller bar which is at rest in the forward position. The one-to-one reciprocating relationship between the puller bar and the magazine means that the two parts move together back and forth at all times for the repeated full stroke of the instrument.
9. The cam bar whose principal purpose is to close the jaws about a clip by means of contact with inclined ramps on either side of jaws when moved rearward is in the forward relaxed position.
10. The safety toggle is rotationally interlocked to the rear of the cam bar and the two move in unison. When drawn rearward, the toggle shifts laterally to engage the puller bar tang by means of an interfacing cam recess molded into the stationary chassis. The purpose of the toggle lock is to maintain force on the cam bar during the return stroke to release potential cold-welding of the contact surfaces between cam and jaws, the result being an inability of the jaws to open and receive an incoming clip. Additional failure events would also occur. The toggle is in the forward disengaged rest position.
11. The stationary mounted, biased lock block rises to engage the puller bar and ceases reciprocating motion following the dispensing of the last closed clip. The jaws are thereby locked open preventing inadvertent closure of empty jaws about a vessel resulting in severance and free bleeding. The cam bar is stacked below the puller bar and the lock block passes through the elongated free space slot with no functional interaction. Locking takes place when the blade of the block is allowed to move upward into the magazine space vacated by the fully advanced ladder. Simultaneously the lower block portion moves into the box port of the puller bar positively impeding reciprocating motion. Concurrently, the loops of the handle are locked in the open position. The block is in a compressed position constrained by the presence of the ladder in the magazine. In movement the ramped hips of the block engage the sides of the elongated slot in the puller bar which cam the lock downward out of contact with the magazine when moving to the rear.

The operational sequence of the clip applier handle as from its beginning status is as follows.
1. Loop handles are in the open position.
2. Linear translator is in the most forward position maintained by force of the return compression spring.
3. Compression spring is in place surrounding the linear translator under slight pre-compression. Full compression is attained when handles are compressed.
4. Anti-backup spring is disengaged and relaxed, and is in position in back of the compression spring.
5. Toggle links connecting the handle loops to the rear of the linear actuator are at the highest pre-compression angle.

Cartridge actuation on the pull stroke is as follows:
1. Puller bar begins movement rearward in concert with the magazine.
2. Magazine forward clip pusher retracts from contact with the clip retained in jaws.
3. Lock block blade, freely projecting through the cam bar, moves into the elongated puller bar slot and the inclined ramps of the lower block portion urge the lock block downward against integral biasing spring and away from contact with the magazine. Condition maintains through full retracting stroke.
4. Puller bar/magazine continues with magazine clawback feature descending to a position between the second clip and the remaining clip stack.
5. Continued rearward movement draws the stack rearward with the magazine.
6. The beginning stack having the advancing ladder in contact with the rearmost clip is now one clip short leaving an empty space in the clip track.
7. The magazine/clip stack in moving rearward leaves the second clip captured in front of the detent feature of the floor in preparation to be picked off and advanced into the jaws on the return stroke.
8. There is a dwell interval in the magazine stroke before the cam bar is engaged. The benefit occurs on the return stroke allowing the advancing next clip to fully enter the open jaws without obstruction.
9. The puller-bar/magazine continues until contacting the cam puller at which time the cam bar joins the rearward stroke.
10. In the remaining cumulative stroke, (a) the forward end of the cam bar engages the inclined ramps on the side of each jaw member urging them together to begin the clip closing phase. (b) The toggle attached to the rear portion of the cam bar is guided laterally into engagement with the puller bar by means of the fixed cam path of the chassis. (c) The forward tip of the cover mounted ladder advancing detent spring enters a port on the rearward moving magazine to fall between rungs of the contained advancing ladder.
11. As pull stroke continues toward completion, the detent spring, fixed to the cover, temporarily arrests the rearward movement of the clip advancing ladder with respect to the continued progress of the magazine. The detent maintains dwell for the specific distance of one clip increment and is raised out of engagement with the ladder' by means of wings on the forward end of the detent riding vertically on cam surfaces straddling the magazine detent port.

12. The ladder is now advanced within the magazine, to place the leading edge in contact with the clawback captured clip stack and closing the empty space generated by the exclusion of the second clip being held forward behind the integral floor detent at the initiation of the pull stroke.

13. The ladder is maintained in this incrementally advanced position by means of engagement with an integral ratchet pawl magazine detent spring preventing reverse movement.

14. The pull stroke moves rearward to completion wherein reversal is prohibited by means of an anti-back feature of the handle. Constraint is released at the end of the stroke allowing return stroke to commence.

15. At the end of the pull stroke, the clip is completely cinched and the clip stack is again made whole.

Handle actuation on the pull stroke is as follows:

1. The handle receives the detachable cartridge and retains it securely in place.

2. The puller bar of the cartridge is engaged to the front wall of the linear actuator.

3. The pull stroke of the handle is initiated by compressing the two handles together.

4. Two opposing toggle links attach to loop handles at their outer ends and meet and couple with the rear portion of the linear translator. Compression of the two loop handles close the angle between the links and imparts a pulling motion to the linear actuator.

5. The pre-loaded compression spring, contacting hips at the front portion of the linear translator, is restrained at the rear by fixed features in the two mating covers. The spring urges the linear translator forward drawing the connected inner link ends with it and forcing the loop handles apart to their starting position. Beginning with the pulling phase, the anti-backup spring is engaged and prevents return motion until stroke is complete. On the return stroke, the anti-backup function is reversed.

6. Reciprocating Motion and forces generated in the handle are imparted to the cartridge by the coupling of the cartridge puller bar to the linear translator of the handle.

Cartridge actuation on the return stroke is as follows:

1. Anti-backup spring in handle is released allowing the compression spring to return the attached cartridge operating components toward an eventual rest position. The slightest initial return movement now releases the closed clip encircling the targeted tissue.

2. Forward moving puller bar tang remains in contact with the toggle imparting a force to the attached cam bar thereby assuring release of a potential friction induced bonding with the jaws.

3. Continuing in the return path, the shorter stroke required for clip closure via cam bar and jaw ramp interaction, is traversed and the toggle disengages allowing the natural springing of the jaws to fully open to receive an incoming clip.

4. At this point in the return stroke, the cam bar, the toggle, and the jaws are disengaged from the puller bar and magazine assembly and have no further function.

5. The magazine moving forward with the cam bar short stroke of Nos (3.) and (4.), allows the fixed ladder advancing detent spring to ride over the magazine top surface first dropping back into the advancing port and bumping over a rung of the advancing ladder, (which is held in a non-returning position by the integral ratchet pawl springs of the magazine) and rising back on top surface to slide for the duration of the remaining stroke.

6. Also at the beginning of the return stroke, the head of the magazine now located behind the second clip (retained by the downwardly flexible floor detent), makes contact and begins its push to place the clip in the jaws thereby leaving an empty post for capture of the leading clip of the approaching clip stack.

7. As the magazine progresses, the clawback feature reaches the end of its cover cam track and rises up to release the clip stack.

8. In continuation, the leading clip of the clip stack depresses and over passes the floor detent to arrive at captured position in preparation for the next advancement the jaws.

9. In completion of the stroke, the forward head of the magazine has picked off the captured clip and transported it into the jaws at the ready for surgical application.

10. Having reached a full return stroke, the magazine and puller are now aligned to allow the last clip lockout block to rise through the two available ports and arrest further reciprocating motion. This can only happen after the last clip is fired and the advancing ladder has moved forward to a non-obstructing position.

11. Repeat pull-push cycle until the entire clip load is expended.

A clip applicator according to the invention has a simplified construction and low cost of manufacture at high production rates, low operating force without recoil, jaw lockout after the last clip, an anti-backup mechanism, and is adaptable for use as a quick snap-in disposable cartridge with a fixed disposable or non-disposable operating handle. An operating handle that provides linear reciprocating motion including scissors-type, pistol grip, and surgical robot may be used in the invention. The applicator according to the invention is adaptable for use with surgical clips in a range of sizes.

Various changes may be made to the structure embodying the principles of the invention. The foregoing embodiments are set forth in an illustrative and not in a limiting sense. The scope of the invention is defined by the claims appended hereto.

I claim:

1. An operating handle for providing linear reciprocating movement to a surgical clip applier having a scissor-type handle and a removable clip applying cartridge comprising a sleeve encasing a chassis and a cover and together defining a datum for cartridge operating components, the chassis defining a channel, the channel having a front end opening for clip applier jaws, a cam bar guide post, a jaw post, a chassis lockout recess, a toggle cam surface, and a rear end opening for a puller bar, a jaws cam bar defined by an elongate strip body having jaw tangs for closing clip applier jaws and having first and second oblong slots, the jaws cam bar placed in the chassis channel with the first oblong slot mounted over the cam bar guide post and the second slot mounted over the jaw post, the jaws cam bar further having a lock out slot, recessed side edges, and an interior sinuous toggle surface, clip applying jaws mounted over the jaw post with the clip applying jaws extending through a front end of the chassis, the clip applying jaws having cam surfaces engaged by the jaw tangs, a safety toggle having a sinuous toggle surface meshed with the toggle cam surface, a puller bar in the form of an elongate plate positioned in the chassis overlying the jaws cam bar, the puller bar having narrow and wide lockout slots and having depending tangs for engaging the jaws cam bar recessed side edges for moving the jaws cam bar for operating the clip applying jaws, the puller bar further having a toggle tang for actuating the safety toggle and having means for delivering linear motion to a clip magazine, and a T-end for receiving linear motion for cartridge operation, a magazine floor plate mounted along a length of the cover and overlying the clip applying jaws and the puller bar, the floor plate having means through which the puller bar delivers linear motion to a clip magazine, the floor plate further having a lockout slot, a clip capture spring, and front end ramps for guiding a clip into the clip applying jaws, a clip magazine overlying the floor plate and defining a clip magazine chamber, a clip stack and a clip advancing ladder in the clip magazine, the clip magazine having means passing by the floor plate and engaging a puller bar means for delivering linear motion for magazine operation, the clip magazine having a lockout slot, at least one detent spring for engaging the clip advancing ladder, a claw back spring for the clip stack, and a clip arm and clip head projecting from a front end of the clip magazine for engaging a clip and pushing it into the clip applying jaws, a cover detent spring mounted on the cover and adapted to pass through the clip magazine lockout slot for restraining movement of the clip advancing ladder, the cover secured to the chassis for enclosing cartridge operating components, the cover having an interior guide surface for aiding movement of clips into the clip applying jaws, and a lockout block positioned in the chassis lockout recess and adapted to pass through the jaws cam bar, the puller bar, the floor plate, and the clip magazine lockout slot to arrest operation of cartridge components after all clips in the clip stack have been used.

* * * * *